nn(12) United States Patent (10) Patent No.: US 11,964,075 B2
Huang et al. (45) Date of Patent: Apr. 23, 2024

(54) INJECTABLE COMPOSITE INKS AND METHODS FOR MAKING AND USING THEREOF

(71) Applicant: University of Florida Research Foundation, Inc., Gainesville, FL (US)

(72) Inventors: Yong Huang, Gainesville, FL (US); Kaidong Song, Gainesville, FL (US); Ashley M. Compaan, Gainesville, FL (US); Wenxuan Chai, Gainesville, FL (US)

(73) Assignee: UNIVERSITY OF FLORIDA RESEARCH FOUNDATION, INCORPORATED, Gainesville, FL (US)

( * ) Notice: Subject to any disclaimer, the term of this patent is extended or adjusted under 35 U.S.C. 154(b) by 434 days.

(21) Appl. No.: 17/150,038

(22) Filed: Jan. 15, 2021

(65) Prior Publication Data
US 2021/0236697 A1 Aug. 5, 2021

Related U.S. Application Data

(60) Provisional application No. 62/962,370, filed on Jan. 17, 2020.

(51) Int. Cl.
*A61L 27/52* (2006.01)
*A61L 27/22* (2006.01)
*A61L 27/36* (2006.01)

(52) U.S. Cl.
CPC ............ *A61L 27/52* (2013.01); *A61L 27/222* (2013.01); *A61L 27/3687* (2013.01); *A61L 2400/06* (2013.01)

(58) Field of Classification Search
CPC .... A61L 27/52; A61L 27/222; A61L 27/3687; A61L 2400/06; A61L 27/48; A61L 27/3804; B33Y 70/00
See application file for complete search history.

(56) References Cited

U.S. PATENT DOCUMENTS

| 6,534,591 B2 | 3/2003 | Rhee et al. |
| 6,548,081 B2 | 4/2003 | Sadozai et al. |
| 2014/0170224 A1* | 6/2014 | Li .......................... A61L 27/38 |
| | | 424/492 |

OTHER PUBLICATIONS

Shin, H.; Olsen, B. D.; Khademhosseini, A. Gellan gum microgel-reinforced cell-laden gelatin hydrogels. J Mater Chem B Mater Biold Med, 1-16. (Year: 2013).*
Benjakul, S.; Kittiphattanabawon, P. Gelatin. Encyclopedia of Food Chemistry, 121-127. (Year: 2019).*
Sakamoto, H.; Kumazawa, Y.; Motoki, M. Strength of Protein Gels Prepared with Microbial Transglutaminase as Related to Reaction Conditions. Journal of Food Science, 59, 4, 866-871. (Year: 1994).*

* cited by examiner

*Primary Examiner* — Jessica Worsham
(74) *Attorney, Agent, or Firm* — ALSTON & BIRD LLP

(57) ABSTRACT

Described herein are injectable composite inks composed of a hydrogel continuous phase with a plurality of microgels present within the hydrogel continuous phase. The inks described herein have unique chemical and physical properties that enable them to be printed into a number of different types of articles. The articles produced by the injectable composite inks have numerous medical applications.

14 Claims, 13 Drawing Sheets

INJECTABLE COMPOSITE INKS AND METHODS FOR MAKING AND USING THEREOF

CROSS REFERENCE TO RELATED APPLICATIONS

This application claims priority to, and the benefit of, U.S. provisional application Ser. No. 62/962,370, filed Jan. 17, 2020 and entitled "Injectable Composite Inks and Methods for Making and Using Thereof," the entire disclosures of which are hereby incorporated herein by reference in their entireties for all purposes.

STATEMENT REGARDING FEDERALLY SPONSORED RESEARCH OR DEVELOPMENT

This invention was made with government support under 1762941 awarded by the National Science Foundation. The Government has certain rights in the invention.

BACKGROUND

Tissue engineering and regenerative medicine are interdisciplinary research areas that apply the principles of materials engineering and life sciences towards the development of technologies that can restore, maintain and improve tissue functions. While tissue or organ transplantation is a generally accepted therapy to treat patients with diseased or failed tissues/organs, this approach is still limited by the challenge of organ donor shortage. Thus, there is a need for improved techniques and methodology for tissue engineering as an alternative to tissue or organ transplantation.

SUMMARY

Described herein are injectable composite inks composed of a hydrogel continuous phase with a plurality of microgels present within the hydrogel continuous phase. The inks described herein have unique chemical and physical properties that enable them to be printed into a number of different types of articles. The articles produced by the injectable composite inks have numerous medical applications.

In one aspect, among others, an injectable composite ink, comprises a hydrogel continuous phase; and a plurality of microgels comprising a hydrogel dispersed within the hydrogel continuous phase. In one or more aspects, the hydrogel of the continuous phase and the hydrogel of the microgel can be the same hydrogel material or can be different hydrogel materials. The hydrogel can comprise chitosan, collagen, gelatin, alginate, hyaluronic acid, heparin, chondroitin sulfate, poly (ethylene glycol) (PEG), and poly (vinyl alcohol), or any combination thereof. The hydrogel continuous phase can be from about 1 wt. % to about 10 wt. % of the injectable composite ink. The microgel can be from about 90 wt. % to about 99 wt. % of the injectable composite ink. The hydrogel continuous phase can comprise gelatin. The gelatin can have a bloom strength of from about 200 to about 350. The gelatin can have an average molecular weight of from about 50,000 to about 100,000.

In various aspects, the microgel can comprise gelatin. The microgel can have an average particle size of from about 100 µM to about 500 µm. The gelatin can be cross-linked. The hydrogel continuous phase can comprise gelatin in the amount of about 1 wt. % to about 10 wt. % of the injectable composite ink, and the microgel can comprise gelatin in the amount of about 90 wt. % to about 99 wt. % of the injectable composite ink. Injectable composite ink can further comprise a cross-linking agent. The cross-linking agent ca comprise transglutaminase. The cross-linking agent can be from about 0.1% w/v to about 5% w/v of the injectable composite ink. The hydrogel continuous phase and microgel can be covalently cross-linked with one another. The injectable composite ink can have a Young's modulus of from about 30 kPa to about 40 kPa. The injectable composite ink can have an injection force of from 0 N to about 25 N. The injectable composite ink liquefies at a temperature greater than 35° C. The injectable composite ink can further comprise a plurality of cells or genes. The cells can comprise fibroblasts. The injectable composite ink can further comprise a bioactive agent.

In another aspect, an injectable composite ink produced by the method comprising admixing a hydrogel and a microgel comprising a hydrogel. The hydrogel and the hydrogel of the microgel can be the same hydrogel material or can be different hydrogel materials. In some aspects, the hydrogel can comprise chitosan, collagen, gelatin, alginate, hyaluronic acid, heparin, chondroitin sulfate, poly (ethylene glycol) (PEG), and poly (vinyl alcohol), or any combination thereof. The hydrogel can be from about 1 wt. % to about 10 wt. % of the injectable composite ink. The microgel can be from about 90 wt. % to about 99 wt. % of the injectable composite ink. The hydrogel can comprise gelatin. The gelatin can have a bloom strength of from about 200 to about 350. The gelatin can have an average molecular weight of from about 50,000 to about 100,000. The microgel can comprise gelatin. The microgel can have an average particle size of from about 100 µm to about 500 µm. The hydrogel can comprise gelatin in the amount of about 1 wt. % to about 10 wt. % of the injectable composite ink, and the microgel can comprise gelatin in the amount of about 90 wt. % to about 99 wt. % of the injectable composite ink.

In various aspects, the method can further comprise admixing a cross-linking agent with the hydrogel and microgel. The agent can comprise transglutaminase. The agent can be from about 0.1% w/v to about 5% w/v of the injectable composite ink. The method can further comprise admixing a plurality of cells or a gene with the hydrogel and microgel. The cells can comprise fibroblasts. The method can further comprise admixing a bioactive agent with the hydrogel and microgel. The method can comprise, after admixing the hydrogel and microgel, heating the admixture at a temperature greater than 30° C.

In another aspect, a method for printing an article comprises printing onto a substrate the injectable composite ink, wherein the injectable composite ink has been liquefied prior to printing on the substrate. The injectable composite ink can be liquefied at a temperature of greater than 35° C. then introduced into the printer. The printer can comprise a three-dimensional (3D) printer. The nozzle of the printer can have a diameter from about 50 µm to about 5 mm. After printing the injectable composite ink on the substrate, the printed article can be cooled at a temperature below about 10° C. When the injectable composite ink includes a cross-linking agent, the printed article can be heated at a temperature greater than 30° C. When the injectable composite ink does not include a cross-linking agent, (a) a cross-linking agent can be applied to the printed article, and (b) the printed ink article can be heated at a temperature greater than 30° C.

In other aspects, an article can comprise the injectable composite ink. An article can be produced by the method. The article can be biocompatible or biodegradable. The article can be a 3D structure. The article can be a 3D lattice, a tube, a cup, a coil or an arch. In another aspect, a method for delivery cells or a gene to a subject comprises administering to the subject the article, wherein the article comprises a plurality of cells or a gene. In one or more aspects, a method for delivering a bioactive agent to a subject comprises administering to the subject the article, wherein the article comprises a bioactive agent. In various aspects, a method for improving wound healing in a subject in need of such improvement can comprise contacting the wound of the subject with the article. In some aspects, a method for reducing or inhibiting adhesion of two tissues in a surgical wound in a subject can comprise contacting the wound of the subject the article. In other aspects, a method for regenerating tissue in a subject can comprise administering to the subject the article.

The advantages of the invention will be set forth in part in the description which follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE DRAWINGS

Many aspects of the present disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

DETAILED DESCRIPTION

Figure 1:
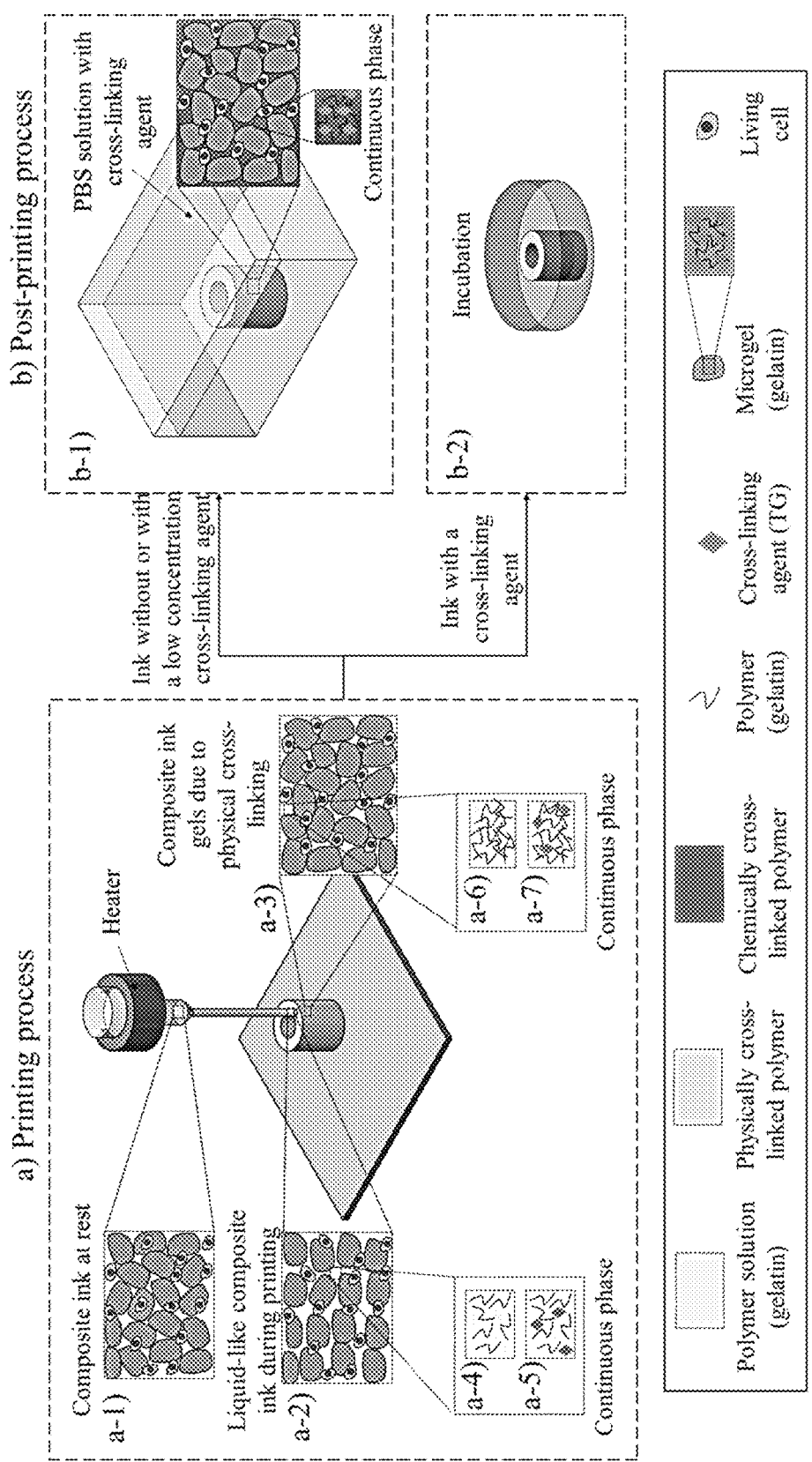
FIG. 1 shows a schematic diagram illustrating an example of direct printing of a gelatin microgel-based composite ink, in accordance with various embodiments of the present disclosure.

Before the present materials, articles and/or methods are disclosed and described, it is to be understood that the aspects described below are not limited to specific compounds, synthetic methods, or uses, as such may, of course, vary. It is also to be understood that the terminology used herein is for the purpose of describing particular aspects only and is not intended to be limiting.

In the specification and in the claims that follow, reference will be made to a number of terms that shall be defined to have the following meanings:

It must be noted that, as used in the specification and the appended claims, the singular forms "a," "an," and "the" include plural referents unless the context clearly dictates otherwise. Thus, for example, reference to "a solvent" includes mixtures of two or more solvents and the like.

"Optional" or "optionally" means that the subsequently described event or circumstance can or cannot occur, and that the description includes instances where the event or circumstance occurs and instances where it does not. For example, the compositions described herein may optionally contain a bioactive agent, where the bioactive agent may or may not be present.

Throughout this specification, unless the context dictates otherwise, the word "comprise," or variations such as "comprises" or "comprising," will be understood to imply the inclusion of a stated element, integer, step, or group of elements, integers, or steps, but not the exclusion of any other element, integer, step, or group of elements, integers, or steps.

As used herein, the term "about" is used to provide flexibility to a numerical range endpoint by providing that a given numerical value may be "a little above" or "a little below" the endpoint without affecting the desired result. For purposes of the present disclosure, "about" refers to a range extending from 10% below the numerical value to 10% above the numerical value. For example, if the numerical value is 10, "about 10" means between 9 and 11 inclusive of the endpoints 9 and 11.

As used herein, the term "admixing" is defined as mixing two or more components together so that there is no chemical reaction or physical interaction. The term "admixing" also includes the chemical reaction or physical interaction between the two or more components.

As used herein, a plurality of items, structural elements, compositional elements, and/or materials may be presented in a common list for convenience. However, these lists should be construed as though each member of the list is individually identified as a separate and unique member. Thus, no individual member of any such list should be construed as a de facto equivalent of any other member of the same list based solely on its presentation in a common group, without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range was explicitly recited. As an example, a numerical range of "about 1" to "about 5" should be interpreted to include not only the explicitly recited values of about 1 to about 5, but also to include individual values and sub-ranges within the indicated range. Thus, included in this numerical range are individual values such as 2, 3, and 4, the sub-ranges such as from 1-3, from 2-4, from 3-5, from about 1-about 3, from 1 to about 3, from about 1 to 3, etc., as well as 1, 2, 3, 4, and 5, individually. The same principle applies to ranges reciting only one numerical value as a minimum or maximum. The ranges should be interpreted as including endpoints (e.g., when a range of "from about 1 to 3" is recited, the range includes both of the endpoints 1 and 3 as well as the values in between). Furthermore, such an interpretation should apply regardless of the breadth or range of the characters being described.

Disclosed are materials and components that can be used for, can be used in conjunction with, can be used in preparation for, or are products of the disclosed compositions and methods. These and other materials are disclosed herein, and it is understood that when combinations, subsets, interactions, groups, etc. of these materials are disclosed, that while specific reference to each various individual combination and permutation of these compounds may not be explicitly disclosed, each is specifically contemplated and described herein. For example, if a hydrogel continuous phase is disclosed and discussed, and a number of different microgels are discussed, each and every combination of hydrogel continuous phase and microgel that is possible is specifically contemplated unless specifically indicated to the contrary. For example, if a class of hydrogel continuous phases A, B, and C are disclosed, as well as a class of microgels D, E, and F, and an example combination of A+D is disclosed, then even if each is not individually recited, each is individually and collectively contemplated. Thus, in this example, each of the combinations A+E, A+F, B+D, B+E, B+F, C+D, C+E, and C+F is specifically contemplated and should be considered from disclosure of A, B, and C; D, E, and F; and the example combination A+D. Likewise, any subset or combination of these is also specifically contemplated and disclosed. Thus, for example, the sub-group of A+E, B+F, and C+E is specifically contemplated and should be considered from disclosure of A, B, and C; D, E, and F; and the example combination of A+D. This concept applies to all aspects of the disclosure including, but not limited to, steps in methods of making and using the disclosed compositions. Thus, if there are a variety of additional steps that can be performed with any specific embodiment or combination of embodiments of the disclosed methods, each such composition is specifically contemplated and should be considered disclosed.

Described herein are injectable composite inks composed of a hydrogel continuous phase with a plurality of microgels present within the hydrogel continuous phase. The injectable composite inks are produced by admixing a hydrogel with a microgel, where the microgel is dispersed throughout the hydrogel, which is referred to herein as the hydrogel continuous phase. The inks described herein have unique chemical and physical properties that enable them to be printed into a number of different types of articles. Provided below are the components used to make the injectable ink compositions as well as methods for making and using the same.

Hydrogel Continuous Phase

The hydrogel continuous phase (HCP) is composed of one or more hydrogels. Hydrogels are hydrophilic polymer networks. Depending upon the selectin of the polymer, the hydrogel can absorb varying amounts of water. In one aspect, the hydrogel includes chitosan, collagen, gelatin, alginate, hyaluronic acid, heparin, chondroitin sulfate, poly (ethylene glycol) (PEG), and poly (vinyl alcohol), or any combination thereof. In another aspect, the hydrogel is a single polymer.

In one aspect, hydrogel continuous phase is gelatin. Gelatin is a water-soluble protein derived from collagen. Gelatin possesses good thermal stability and biodegradability. In one aspect, the gelatin used to produce the hydrogel continuous phase has a bloom strength of from about 200 to about 350, or about 200, about 210, about 215, about 220, about 225, about 230, about 235, about 240, about 245, about 250, about 255, about 260, about 265, about 270, about 275, about 280, about 285, about 290, about 295, about 300, about 305, about 310, about 315, about 320, about 325, about 330, about 335, about 340, about 345, or about 350, where any value can be a lower and upper endpoint of a range (e.g., about 210 to about 280, about 220 to about 230, etc.).

In one aspect, the gelatin used to produce the hydrogel continuous phase has an average molecular weight of from about 10,000 to about 150,000, or about 10,000, about 20,000, about 30,000, about 40,000, about 50,000, about 60,000, about 70,000, about 80,000, about 90,000, about 100,000, about 110,000, about 120,000, about 130,000, about 140,000, about 150,000, where any value can be a lower and upper endpoint of a range (e.g., about 20,000 to about 120,000, about 50,000 to about 100,000, etc.).

In one aspect, the gelatin is type A gelatin having a 225 bloom strength manufactured by MP Biomedicals, LLC (CAS #9000-70-8 derived from porcine skin).

Microgels

The injectable inks described herein include a plurality of microgels dispersed throughout the hydrogel continuous phase. The microgel can be prepared using a number of techniques. In one aspect, the hydrogel used to produce the microgel can be dispersed or dissolved in a solvent and subsequently micronized. The size of the microgels can be modified by varying the concentration of hydrogel that is micronized and the duration of micronization. In one aspect, the concentration of the hydrogel is from about 1% w/v to about 20% w/v in water or buffered solution prior to micronization. In another aspect, the concentration of the hydrogel is from about 1% w/v, about 2% w/v, about 3% w/v, about 4% w/v, about 5% w/v, about 6% w/v, about 7% w/v, about 8% w/v, about 9% w/v, about 10% w/v, about 11% w/v, about 12% w/v, about 13% w/v, about 14% w/v, about 15% w/v, about 16% w/v, about 17% w/v, about 18% w/v, about 19% w/v, or about 20% w/v, where any value can be a lower and upper endpoint of a range (e.g., about 3% w/v to about 18% w/v, about 5% w/v to about 15% w/v, etc.).

In another aspect, the microgel has an average particle size of from about 100 μm to about 500 μm, or about 100 μm, about 125 μm, about 150 μm, about 200 about 225 μm, about 250 μm, about 300 μm, about 325 μm, about 350 μm, about 375 μm, about 400 μm, about 425 μm, about 450 μm, about 475 μm, or about 500 μm, where any value can be a lower and upper endpoint of a range (e.g., about 100 μm to about 350 μm, etc.). Non-limiting procedures for making the microgels described herein are provided in the Examples.

The hydrogel used to produce the microgels are composed of one or more hydrogels. In one aspect, the hydrogel includes chitosan, collagen, gelatin, alginate, hyaluronic acid, heparin, chondroitin sulfate, poly (ethylene glycol) (PEG), and poly (vinyl alcohol), or any combination thereof. In another aspect, the hydrogel is a single polymer.

In one aspect, the hydrogel of the continuous phase and the hydrogel of the microgel are the same hydrogel material.

In another aspect, the hydrogel of the continuous phase and the hydrogel of the microgel are different hydrogel materials.

In one aspect, the hydrogel used to produce the microgel is gelatin. In one aspect, the gelatin used to produce the microgel has a bloom strength of from about 200 to about 350, or about 200, about 210, about 215, about 220, about 225, about 230, about 235, about 240, about 245, about 250, about 255, about 260, about 265, about 270, about 275, about 280, about 285, about 290, about 295, about 300, about 305, about 310, about 315, about 320, about 325, about 330, about 335, about 340, about 345, or about 350, where any value can be a lower and upper endpoint of a range (e.g., about 210 to about 280, about 220 to about 230, etc.).

In one aspect, the gelatin used to produce the microgel has an average molecular weight of from about 10,000 to about 150,000, or about 10,000, about 20,000, about 30,000, about 40,000, about 50,000, about 60,000, about 70,000, about 80,000, about 90,000, about 100,000, about 110,000, about 120,000, about 130,000, about 140,000, about 150,000, where any value can be a lower and upper endpoint of a range (e.g., about 20,000 to about 120,000, about 50,000 to about 100,000, etc.).

In one aspect, the gelatin is type A gelatin having a 225 bloom strength manufactured by MP Biomedicals, LLC (CAS #9000-70-8 derived from porcine skin).

In one aspect, a cross-linking agent can be admixed with the hydrogel used to produce the microgel. The cross-linking agent is any compound that facilitates covalent or non-covalent cross-linking of the hydrogel used to produce the microgel.

In one aspect, the cross-linking agent can be prepared in a solution of water or buffered solution, and the resulting solution of cross-linking agent can be added to a solution of the hydrogel and subsequently mixed using techniques known in the art. After mixing the hydrogel and cross-linking agent, the mixture can be heated to further promote cross-linking. In one aspect, the mixture is heated at a temperature greater than 30° C., or from about 30° C. to about 50° C., or from about 35° C. to about 40° C. The cross-linking agent can be subsequently deactivated by heating the enzyme at a sufficient temperature.

In one aspect, the cross-linking agent is an enzyme that catalyzes the formation of isopeptide bonds between proteins. In another aspect, the cross-linking agent comprises a transglutaminase. Non-limiting procedures for making the microgels described herein are provided in the Examples.

Methods for Preparing the Injectable Ink Compositions

The injectable composite inks described herein are produced admixing a hydrogel and a microgel comprising a hydrogel, whereupon the microgel is dispersed throughout the hydrogel continuous phase. In one aspect, the microgel is mixed with the hydrogel, where the hydrogel is in dry powder form. In another aspect, the microgel is mixed with the hydrogel, where the hydrogel is in dry powder form, and the admixture is subsequently heated at a temperature sufficient to solubilize the hydrogel powder. The temperature and duration at which the admixture is heated can vary depending upon the selection of the hydrogel selected. The hydrogel and microgel can be admixed using techniques known in the art. In one aspect, the hydrogel and microgel are admixed for a sufficient time to ensure the microgel is homogeneously dispersed throughout the hydrogel (i.e., hydrogel continuous phase). Non-limiting procedures for making the injectable composite inks described herein are provided in the Examples.

In one aspect, the hydrogel used to produce the hydrogel continuous phase is from about 1 wt. % to about 10 wt. % of the injectable composite ink, or about 1 wt. %, about 2 wt. %, about 3 wt. %, about 4 wt. %, about 5 wt. %, about 6 wt. %, about 7 wt. %, about 8 wt. %, about 9 wt. %, or about 10 wt. % of the injectable composite ink, where any value can be a lower and upper endpoint of a range (e.g., about 1 wt. % to about 5 wt. %, etc.). In another aspect, the microgel is from about 90 wt. % to about 99 wt. % of the injectable composite ink, or about 90 wt. %, about 91 wt. %, about 92 wt. %, about 93 wt. %, about 94 wt. %, about 95 wt. %, about 96 wt. %, about 97 wt. %, about 98 wt. %, or about 99 wt. % of the injectable composite ink, where any value can be a lower and upper endpoint of a range (e.g., about 95 wt. % to about 99 wt. %, etc.).

In another aspect, the hydrogel used to produce the hydrogel continuous phase comprises gelatin in the amount of about 1 wt. % to about 10 wt. % of the injectable composite ink, and the microgel comprises gelatin in the amount of about 90 wt. % to about 99 wt. % of the injectable composite ink.

One or more additional components can be admixed with the hydrogel and microgel. In one aspect, a cross-linking agent as provided above can be admixed with the hydrogel used to produce the hydrogel continuous phase and the microgel in order to covalently cross-link the hydrogel continuous phase with the microgel. In one aspect, the cross-linking agent is from about 0.1% w/v to about 5% w/v of the injectable composite ink, or is about 0.1% w/v, about 0.5% w/v, about 1% w/v, about 1.5% w/v, about 2% w/v, about 2.5% w/v, about 3% w/v, about 3.5% w/v, about 4% w/v, about 4.5% w/v, about 5% w/v of the injectable composite ink, where any value can be a lower and upper endpoint of a range (e.g., about 1% w/v to about 4% w/v, etc.). In one aspect, the cross-linking agent can be prepared in a solution of water or buffered solution, and the resulting solution of cross-linking agent can be added to a liquefied form of the injectable composite ink.

In other aspects, the injectable composite inks described herein can hold and/or encapsulate live cells for delivery to a subject. In one aspect, the cells are suspended in a liquefied form of the injectable composite ink. Non-limiting procedures for incorporating live cells into the injectable composite inks described herein are provided in the Examples.

In one aspect, any of the injectable composite inks described herein can include living cells or genes. Examples of living cells include, but are not limited to, fibroblasts, hepatocytes, chondrocytes, stem cells, bone marrow, muscle cells, cardiac myocytes, neuronal cells, or pancreatic islet cells. Any of the cells and genes disclosed in U.S. Pat. No. 6,534,591 B2, which is incorporated by reference in its entirety, can be used.

In another aspect, the injectable composite inks described herein can be used as a carrier and delivery device for a wide variety of releasable bioactive agents having curative or therapeutic value for human or non-human animals. Included among bioactive agents that are suitable for incorporation into the composites described herein are therapeutic drugs, e.g., anti-inflammatory agents, anti-pyretic agents, steroidal and non-steroidal drugs for anti-inflammatory use, hormones, growth factors, contraceptive agents, antivirals, antibacterials, antifungals, analgesics, hypnotics, sedatives, tranquilizers, anti-convulsants, muscle relaxants, local anesthetics, antispasmodics, antiulcer drugs, peptidic agonists, sympathiomimetic agents, cardiovascular agents, antitumor agents, oligonucleotides and their analogues and so forth.

Methods for Preparing Articles from the Injectable Composite Inks

The injectable composite inks described herein possess several physical properties that make them amenable to printing on a substrate to produce three dimensional articles. The injectable composite inks are easy to inject. In one aspect, the injectable composite ink has an injection force of from 0 N to about 25 N, or about 1 N, about 2 N, about 3 N, about 4 N, about 5 N, about 6 N, about 7 N, about 8 N, about 9 N, about 10 N, about 12 N, about 14 N, about 16 N, about 18 N, about 120 N, about 22 N, or about 25 N, where any value can be a lower and upper endpoint of a range (e.g., about 5 N to 15 N, etc.). In another aspect, injectable composite ink can be injected through a nozzle having a diameter from about 50 µm to about 5 mm, about 50 µm to about 2 mm, about 75 µm to about 1000 µm, about 100 µm to about 750 µm, about 100 µm to about 400 µm, or about 100 µm, about 150 µm, about 200 µm, about 250 µm, about 300 µm, about 350 µm, about 400 µm, about 450 µm, about 500 µm, about 600 µm, about 700 µm, about 800 µm, about 900 µm, about 1000 µm, about 2 mm, about 3 mm, about 4 mm, or about 5 mm, where any value can be a lower and upper endpoint of a range (e.g., about 200 µm to about 300 µm, etc.). The Examples provide additional rheological data of the injectable composite inks described herein.

The methods described herein use printers to print the injectable composite ink on a surface of a substrate. In one embodiment, the printer is an ink-jet printer. Ink-jet printers useful herein can be two-dimensional or three-dimensional printers, for example, FUJIFILM Dimatix Materials Printer DMP-2850, Mimaki® UJF-6042 Flatbed UV Printer (Mk1 or Mk2), Mimaki® UJV500-160, or Hyrel 3D printer.

In one aspect, the injectable composite ink is liquefied prior to printing on the substrate. In this aspect, the injectable composite ink is heated at a sufficient temperature and time to liquefy the ink, the liquefied ink is transferred to reservoir in the printer. In one aspect, the injectable composite ink can be heated at a temperature greater than 35° C., or from about 35° C. to about 50° C., or from about 35° C. to about 40° C. Depending upon the article to be printed, the diameter of the nozzle can vary. The Examples provide additional parameters for printing different types of articles.

The substrate that is selected can vary depending upon the application of the printed article. In one aspect, the substrate is made of plastic or glass. In certain aspects, the printed article is removed from the substrate such as, for example, peeling the printed article from the substrate. In other aspects, the substrate can be a medical implant, where the injectable composite ink is printed on the implant and not removed from the implant.

In one aspect, the printed article (with or without the substrate) is cooled in order to further promote gelation. In one aspect, the printed article is cooled to a temperature below 10° C., or from about 0° C. to 10° C.

In one aspect, when the injectable composite ink includes a cross-linking agent, the printed article can be heated at a temperature greater than 30° C. In another aspect, the printed article can be heated at a temperature greater than 30° C., or from about 30° C. to about 50° C., or from about 35° C. to about 40° C.

In another aspect, when the injectable composite ink does not include a cross-linking agent, a cross-linking agent can be applied to the printed ink composite followed by heating the printed ink composite at a temperature greater 30° C.

The shape of the printed article can vary depending upon the application of the article. In one aspect, the article is a three-dimensional (3D) structure such as, for example, a 3D lattice, a tube, a cup, a coil, or an arch. In the case when the printed article is to be used in medical applications, the article is biocompatible and/or biodegradable. In one aspect, the injectable composite ink has a Young's modulus of from about 30 kPa to about 40 kPa. Not wishing to be bound by theory, the relatively low Young's modulus makes articles and structure produced from the injectable composite inks more flexible, which makes them useful in medical applications where the articles will be implanted in a subject.

Applications of Printed Articles

The printed articles produced by the injectable composite inks described herein can be used for a variety of uses related to drug delivery, small molecule delivery, wound healing, burn injury healing, and tissue regeneration. The printed articles are useful for situations which benefit from a hydrated, pericellular environment in which assembly of other matrix components, presentation of growth and differentiation factors, cell migration, or tissue regeneration are desirable.

The printed articles described herein can be placed directly in or on any biological system without purification as it is composed of biocompatible materials. Examples of sites the printed articles can be placed include, but not limited to, soft tissue such as muscle or fat; hard tissue such as bone or cartilage; areas of tissue regeneration; a void space such as periodontal pocket; surgical incision or other formed pocket or cavity; a natural cavity such as the oral, vaginal, rectal or nasal cavities, the cul-de-sac of the eye, and the like; the peritoneal cavity and organs contained within, and other sites into or onto which the compounds can be placed including a skin surface defect such as a cut, scrape or burn area.

The printed articles described herein can be used in a number of different surgical procedures. In one aspect, the composites and compositions can be used in any of the surgical procedures disclosed in U.S. Pat. Nos. 6,534,591 B2 and 6,548,081 B2, which are incorporated by reference in their entireties. In one aspect, the printed articles described herein can be used in cardiosurgery and articular surgery; abdominal surgery where it is important to prevent adhesions of the intestine or the mesentery; thoracic surgery involving the lungs and heart (e.g., heart bypass or transplant surgery); operations performed in the urogenital regions where it is important to ward off adverse effects on the ureter and bladder, and on the functioning of the oviduct and uterus; and nerve surgery operations where it is important to minimize the development of granulation tissue. In surgery involving tendons, there is generally a tendency towards adhesion between the tendon and the surrounding sheath or other surrounding tissue during the immobilization period following the operation. In another aspect, the printed articles described herein can be used to prevent adhesions after laparoscopic surgery, pelvic surgery, oncological surgery, sinus and craniofacial surgery, ENT surgery, or in procedures involving spinal dura repair.

In another aspect, the printed articles can be used in ophthalmological surgery. In ophthalmological surgery, a biodegradable implant could be applied in the angle of the anterior chamber of the eye for the purpose of preventing the development of synechiae between the cornea and the iris; this applies especially in cases of reconstructions after severe damaging events. Moreover, degradable or permanent implants are often desirable for preventing adhesion after glaucoma surgery and strabismus surgery.

In another aspect, the composites and compositions described herein can be used for the augmentation of soft or hard tissue. In another aspect, the composites and compositions described herein can be used to coat implants. In another aspect, the composites and compositions described herein can be used to treat aneurisms.

In another aspect, the printed articles described herein can be used for the augmentation of soft or hard tissue. In another aspect, the printed articles described herein can be printed on implants. In another aspect, the printed articles described herein can be used to treat aneurisms.

The printed articles herein can be used as a carrier and delivery device for a wide variety of bioactive agents having curative or therapeutic value for human or non-human animals. Any of the bioactive agents described above can be used in this aspect.

In one aspect, the printed articles described herein can be used for the delivery of living cells to a subject. Any of the living cells described above can be used in the aspect.

In one aspect, the printed articles can be used for the delivery of growth factors and molecules related to growth factors.

In one aspect, described herein are methods for reducing or inhibiting adhesion of two tissues in a surgical wound in a subject by contacting the wound of the subject with a printed article as described herein.

In another aspect, described herein are methods for improving wound healing in a subject in need of such improvement by contacting a wound of a subject in need of wound healing improvement with a printed article as described herein.

The printed articles can be used for treating a wide variety of tissue defects in an animal, for example, a tissue with a void such as a periodontal pocket, a shallow or deep cutaneous wound, a surgical incision, a bone or cartilage defect, and the like.

The injectable composite inks described herein can be applied to an implantable device such as a suture, clamp, prosthesis, catheter, metal screw, bone plate, pin, a bandage such as gauze, and the like, to enhance the compatibility and/or performance or function of an implantable device with a body tissue in an implant site. The injectable composite inks can be printed or applied to an implantable device.

It is understood that the printed articles can be applied to a subject in need of tissue regeneration. For example, cells can be present in the printed article described herein for implantation. Examples of subjects that can be treated with the composites described herein include mammals such as mice, rats, cows or cattle, horses, sheep, goats, cats, dogs, and primates, including apes, chimpanzees, orangutans, and humans. In another aspect, the composites and compositions described herein can be applied to birds. When being used in areas related to tissue regeneration such as wound or burn healing, it is not necessary that the printed articles eliminate the need for one or more related accepted therapies.

EXAMPLES

The following examples are put forth so as to provide those of ordinary skill in the art with a complete disclosure and description of how the compounds, compositions, and methods described and claimed herein are made and evaluated and are intended to be purely exemplary and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. Numerous variations and combinations of reaction conditions (e.g., component concentrations, desired solvents, solvent mixtures, temperatures, pressures, and other reaction ranges and conditions) can be used to optimize the product purity and yield obtained from the described process. Only reasonable and routine experimentation will be required to optimize such process conditions.

Preparation of Injectable Composite Ink

For the preparation of a gelatin-based microgel, 10.5% w/v gelatin (e.g., 225 bloom type A, from porcine skin, MP Biomedicals, Solon, Ohio) powder can be dissolved in phosphate buffered saline (e.g., PBS, Corning cellgro, Manassas, Va.) at 37° C. in a bead bath for 30 minutes. 20.0% w/v transglutaminase (TG) (e.g., Moo Gloo TI Transglutaminase Formula, Modernist Pantry, York, Me.) stock solution can be prepared by dissolving TG powder in PBS and vortexing gently then incubating in a 37° C. bead bath for 30 minutes. These two solutions can then be mixed at a 19:1 ratio for final concentrations of 10.0% w/v gelatin and 1.0% TG. Then the mixed solution can be incubated in a 37° C. bead bath for 4 hours for gelatin cross-linking. Both 5.0% and 15.0% w/v gelatin gels can be prepared analogously, keeping a gelatin to TG ratio of 10:1 (TG concentrations were 0.5% and 1.5% w/v accordingly). The cross-linked gelatin gel can then be heated in a 100° C. water bath for 30 minutes to deactivate the TG. Finally, the cross-linked gel can be blended using a blender (e.g., a 3-speed hand blender, KitchenAid, Benton Harbor, Mich.) at the highest speed for 5 minutes with 200 mL deionized (DI) water added in the blending jar. After blending the microgel mixture can be centrifuged at 4,200 rpm for 5 minutes to remove the extra water. Then, the packed microgels can be combined with an equal volume of PBS and autoclaved at 121° C. for 60 minutes. The sterilized microgels can be recollected by centrifuging at 4,200 rpm for 5 minutes and stored at 4° C. refrigerator until use, and after sterilization, microgels should be handled in a biosafety cabinet using aseptic technique.

For the preparation of the injectable composite ink, the gelatin microgels can be mixed with 3% w/v gelatin dry powders. The mixture can be mixed thoroughly with a glass rod and then incubated in a 37° C. bead bath for 30 minutes until the gelatin powder was completely dissolved. The composite ink can then be loaded in a printer cartridge assembled with a heated print head for acellular structure printing. For mechanical testing, stocked TG was added to the composite ink to reach a final concentration of 0.5% w/v TG immediately before casting. A gelatin-based microgel was prepared for printing using this method.

Printing Systems and Printing Protocols

Referring to FIG. 1, shown is a schematic diagram illustrating direct printing of a gelatin microgel-based composite ink. An example of direct printing of gelatin microgel-based composite ink is shown. A method is depicted in (a) of FIG. 1 for composite ink direct printing in air. Beginning at (a-1) of FIG. 1, Composite ink can be stored in a dispensing syringe. Composite ink in (a-2) of FIG. 1 passes through a nozzle and undergoes shear-thinning and in (a-3) of FIG. 1 the composite ink solidifies immediately after deposition due to physical cross-linking. The composite ink (for example, gelatin-based herein) can be in a form as shown in (a-4) of FIG. 1 without a cross-linking agent and can be in a form as shown in (a-5) of FIG. 1 with a cross-linking agent (for example, TG herein). Physically cross-linked polymer (gelatin), as shown in (a-6) of FIG. 1 without the cross-linking agent and as shown in (a-7) of FIG. 1 with the cross-linking agent (TG), forms the printed object. A method is depicted in (b) of FIG. 1 for a post-printing process. At schematic (b-1) of FIG. 1, cross-linking is shown in a cross-linking agent bath for structures printed from inks without cross-linking agent and at schematic (b-2) of FIG. 1 cross-linking is shown in an incubation environment for structures printed from inks with cross-linking agent.

Extrusion printing using the microgel-based composite ink was carried out for evaluation. All extrusion printing works were conducted through a ball screw motion controlled microdispensing machine (e.g., Hyrel Engine SR, Hyre13D, Norcross, Ga.) with warm flow heads (e.g., KRA-15, Hyrel3D, Norcross, Ga.). The temperature for the ink reservoir was set to 32° C. for structures printing. A 22 gauge (0.41 mm inner diameter) dispensing tip (e.g., EFD Nordson, Vilters, Switzerland) was used to print the acellular structures. The layer height was set to 0.40 mm and the flow rate multiplier was 1.0. All structures were printed using a tip travel speed of 3 mm/second. After printing, the structures were placed in a refrigerator at 4° C. for at least 30 minutes for thermal gelation. Then chilled constructs were treated with TG in PBS at 30° C. for covalent cross-linking to form physiologically stable constructs.

A 25 gauge (0.25 mm inner diameter) dispensing tip (e.g., EFD Nordson, Vilters, Switzerland) was used to print the cellular tube structure. The layer height was set as 0.25 mm and the flow rate multiplier was 1.0. The moving speed of the tip was 2 mm/second. After printing, the structures were put into a 37° C. bead bath for 30 minutes for covalent cross-linking to form physiologically stable constructs since TG was already mixed with the composite ink.

To evaluate the printability, all of the printing path codes were programmed manually (e.g., as custom G-code scripts). For the complex 3D structure printing, all of the 3D structure models were designed through SolidWorks (Dassault Systemes SolidWorks Corp, Waltham, Mass.) and exported as STL files. The STL files were prepared using the Slicer tools embedded in the Repetrel control software of the Hyrel 3D printer. The G-code was generated automatically after slicing.

Rheological Property Measurement

Rheological properties of the gelatin-based microgel composite ink with 5% gelatin microgels, 10% gelatin microgels and 15% gelatin microgels were measured using a rheometer (e.g., MCR 702 TwinDrive, Anton Paar, Ashland, Va.) with a sandblasted parallel measuring geometry (e.g., a diameter of 25 mm, a plate-to-plate gap of 1 mm, and a plate roughness of 4.75 μm). Strain sweeps (strain range: 1% to 100%) were performed at a low frequency (1 Hz) for the gelatin-based microgel composite ink formulations to determine the linear viscoelasticity region (LVR) and the yield stress value. Samples were pre-sheared at 100 s$^{-1}$ for 30 seconds followed by waiting for a 60 second recovery period to eliminate loading effects. 1851 Steady rate sweeps were conducted (shear rate range: 0.01 s$^{-1}$ to 100 s$^{-1}$) at a low strain (1%) to confirm the shear-thinning property of the composite ink. To explore the transition between solid-like and fluid-like behavior, the gelatin-based microgel composite inks were characterized using cyclic oscillatory shear between 1% and 100% strain at low frequency (1 Hz) for 300 seconds at each strain amplitude. For the sol-gel transition behavior investigation, the composite ink was characterized using a temperature sweep at a scanning rate of 0.01° C./second and time sweep at a low frequency (1 Hz) and low strain (1%). For the response time of viscosity after shearing, the gelatin microgel-based composite ink was pre-sheared at a shear rate of 100 s$^{-1}$ for 10 seconds after which the shear rate was reduced to 1 s$^{-1}$ and the viscosity change was recorded during the following 10 seconds.

Mechanical Property Measurement

Mechanical properties of the gelatin-based microgel composite ink were measured separately using a micro tester (eXpert 4000, admet, Norwood, NA). The composite ink formulations with 5% gelatin microgels, 10% gelatin microgels, and 15% gelatin microgels were cast in dog-bone shaped PDMS molds with a cross-section of 1.60 mm×2.00 mm 2 and an equivalent structure was printed using the composite ink formulation with 10% gelatin microgels for comparison. All of the tensile tests were performed at a jog rate of 1 mm/second. The load data was collected using the 1,000 g load sensor and the motion stopped at the 90% of the maximum load. The stress-strain curve was generated according to the load, displacement and sample shape. The Young's Modulus of the gelatin microgel-based composite inks was calculated through the linear region of the stress-strain curve.

Gelatin Particle Size Measurement

Particle sizes of the gelatin microgels were measured using a particle characterization machine (e.g., LS320, Beckman Coulter, Brea, Calif.) based on laser light scattering. A 10% gelatin gel blended for 3 minutes, 5 minutes, and 7 minutes was characterized to illustrate the effect of the blending time. Also, 5% gelatin, 10% gelatin, and 15% gelatin gels, blended for 5 minutes, were characterized to determine the relationship between microgel size and gelatin concentration. Each sample type was measured in triplicate with a measurement time of 60 seconds.

Water Content and Volume Shrinkage

To examine the water content of the designed composite inks, already cross-linked 5% gelatin, 10% gelatin and 15% gelatin composite ink were immersed into phosphate buffered saline (PBS) for 1 hour at 37° C. to ensure complete hydration. Then the composite inks were removed from PBS and placed in Petri dishes and dried at 37° C. for 24 hours, and finally weighted to determine the dry weights of each of the composite inks. The water content of the designed composite inks was determined from the weight differences of inks before and after drying process:

$$\text{Water content} = \frac{W_{wetting} - W_{drying}}{W_{drying}} \quad (1)$$

where $W_{wetting}$ is the weight of the designed composite ink after gelation and immersion at 37° C., and $W_{wetting}$ is the dry weight of the composite ink. The mass of residual salt from PBS is negligible when compared to the mass of the polymer. The volume shrinkage (%) of the designed composite ink was defined as the percentage of water volume loss after 24 hours drying process.

$$\text{Volume shrinkage (\%)} = \quad (2)$$
$$-\left(1 - \frac{V_i - V_{H_2O}}{V_i}\right) \times 100\% = -\left(1 - \frac{V_w}{V_i}\right) \times 100\% = -\frac{V_{H_2O}}{V_i} \times 100\%$$

where $V_i$ is the volume of initial composite ink, $V_{H_2O}$ is the volume of the water loss, and $V_w$ is the volume of water after drying process.

Cellular Structure

A cellular ink was prepared by suspending NIH 3T3 mouse fibroblasts (e.g., ATCC, Rockville, Md.) in the warm gelatin-based microgel composite ink with a final concentration of $1\times10^5$ cells/mL. 3T3 mouse fibroblasts cells were prepared as follows. 3T3 cells were cultured in Dulbecco's Modified Eagle Medium (DMEM) (e.g., Sigma Aldrich, St. Louis, Mo.) supplemented with 10% Fetal Bovine Serum (FBS) (e.g., HyClone, Logan, Utah) in a humidified 5% $CO_2$ incubator (e.g., VWR, Radnor, Pa.) at 37° C., and the culture medium was replaced every three days as required. Freshly 90% confluent flasks of 3T3 fibroblasts were washed twice with PBS and incubated with 0.25% Trypsin/EDTA (e.g., Sigma Aldrich, St. Louis, Mo.) for 5 minutes at 37° C. to detach the cells from the culture flasks. Then the cell suspension was centrifuged at 1000 rpm for 5 minutes at room temperature, and the resulting pellet was resuspended in DMEM complete cell culture medium with 1.0% penicillin and streptomycin (e.g., Sigma Aldrich, St. Louis, Mo.). The re-suspended cells were adjusted to the cell concentration of $1\times10^7$ cells/mL as stock and added to the warmed ink mixture to produce inks with final concentrations of 3% gelatin and $1\times10^5$ cells/mL in packed 5% (w/v), 10% (w/v), and 15% (w/v) gelatin microgels respectively. TG stock was added to the composite ink to reach the final concentration of 0.5% w/v TG immediately before cellular structure printing. The cellular ink was loaded in a sterilized KRA-15 cartridge for printing. Printing parameters for cellular structures are specified before.

The printed 10% gelatin microgel composite with 3T3 cellular structures were put into a 24-well plate and incubated for 45 minutes at 37° C. in a humidified 5.0% $CO_2$ incubator for gelatin-TG cross-linking. After cross-linking, the printed cellular structures were cultured in a complete cell culture medium with 1.0% penicillin and streptomycin in a humidified 5.0% $CO_2$ incubator at 37° C., with the culture medium replaced every other day. The cell morphology within the constructs was evaluated on day 0 and day 14 using fluorescent staining. The cellular structures were washed twice with PBS and then stained with a final concentration of 10 µg/mL Hoechst 33342 (e.g., Sigma-Aldrich, St. Louis, Mo.) to stain nuclei blue and a final concentration of 10 µg/mL fluorescein diacetate (FDA) (e.g., Sigma-Aldrich, St. Louis, Mo.) to stain live cells green. After incubation in the dark for 5 minutes at room temperature, the cellular structures were imaged using the green fluorescent, and blue fluorescent channels of a fluorescence microscope (e.g., EVOS FL, ThermoFisher Scientific, Waltham, Mass.) at 4× or 10× magnification.

For metabolic activity quantification in the printed cellular structures and cast cellular structures, 100 µL of 5%, 10%, and 15% cellular ink with $1\times10^5$ cells/mL, respectively, were printed or cast in a 96-well plate. After incubation for 45 minutes in a 37° C. bead bath for cross-linking the specimens, the specimens were cultured in a complete cell culture medium with 1.0% penicillin and streptomycin in a humidified 5.0% $CO_2$ incubator at 37° C. The cellular structures were evaluated using the AlamarBlue assay (e.g., ThermoFisher Scientific, Waltham, Mass.) on Days 1, 3, and 5 per the manufacturer's protocol. Briefly, on each testing day, the cell medium was removed, and then 80 µL cell medium with 10% (v/v) AlamarBlue was added in each well and incubated for 2 hours. The reducing activity, which correlates to the population of living cells was quantitatively measured with a fluorescence microplate reader (e.g., Synergy HT, Biotek, Winooski, Vt.). The circularity of cells in the printed and cast samples was measured based on the cell morphology on Day 1, 3, 5, and 7 by outlining isolated cells with ImageJ (e.g., NIH, Bethesda, Md.) for more than 50 cells per condition.

Statistical Analysis

All quantitative values in the text and figures were reported as means±standard deviation (SD) with n=3 samples per group. Statistical analysis was performed using analysis of variance (ANOVA), and p values of less than 0.05 were considered statistically significant.

Composite Ink Characterization

Gelatin-Gelatin Composite Ink Properties

As introduced, gelatin is a water-soluble protein derived from collagen. Due to its good biocompatibility and biodegradability and ability to form hydrogels, gelatin is widely used in applications ranging from the food industry to medicine and tissue engineering. Gelatin can form physical hydrogels via physical interactions between helical regions of the protein. The thermoreversible hydrogel formed by aqueous gelatin has an upper critical solution temperature (UCST) of 25-35° C. When the temperature exceeds the critical point, the hydrogel will liquefy as the helical region becomes random coils. While attempts have been made to exploit the sol-gel transition of this thermoreverible material for 3D bioprinting such that it transitions from a low viscosity fluid (inside the dispensing tip) to physically cross-linked hydrogel (outside the dispensing tip), the process is too quick to control during printing, which results in a poor print fidelity. In order to address this during the printing process, the ink formulation can be adjusted to improve printability.

Jammed gelatin-based microgels have been chosen as the rheology modifier since the gelatin-based microgels have the same cell-responsive characteristics as the continuous phase (gelatin). To form gelatin-based constructs which are stable at physiological conditions, a variety of cross-linking methodologies and chemistries have been developed. One of the mildest and most convenient cross-linking reactions relies on microbial TG, an enzyme which is highly active at physiological conditions and catalyzes the formation of covalent bonds between protein molecules. Here, TG was used as the physiological cross-linking agent to produce a thermostable final structure so that the printed structures are suitable for tissue engineering and regenerative medicine applications including implantation.

An example of the overall process for printing constructs using gelatin-based microgel composite ink is illustrated in FIG. 1. Before printing, gelatin microgels in the composite ink are restricted as jammed as shown in (a-1) of FIG. 1 through physical interactions with surrounding microgels, resulting in solid-like behavior. When the ink passes through the extrusion nozzle tip, it is subjected to sufficient shear stress, which liquefies the composite ink (a-2 of FIG. 1) and enables smoothly flowing deposition in controlled spatial patterns. After deposition, the unjammed liquid-like microgels within the composite mixture recover to solid-like behavior and retain the printed configuration (a-3 of FIG. 1). For gelatin-based composite ink development, the continuous gelatin solution phase may include TG as a cross-linking agent during the ink preparation phase if the printing time is short enough, typically 45 minutes, for the composite ink to maintain its yield-stress property during the TG-initiated cross-linking process. (a-4) and (a-5) of FIG. 1 show the continuous gelatin phase of the composite ink without or with TG, respectively, during printing, and (a-6) and (a-7) of FIG. 1 show the continuous gelatin phase of the composite ink without or with TG, respectively, after printing.

During the post-printing process (b of FIG. 1), if the continuous gelatin phase does not include TG, the printed structure is immersed in a TG solution for the chemical cross-linking of the continuous phase (b-1 of FIG. 1); if the continuous gelatin phase includes TG, the printed structure is directly incubated at 37° C. for further chemical cross-linking (b-2 of FIG. 1).

Assessment of Self-Supporting Property of Gelatin-Based Microgel Composite Ink

Figure 2:
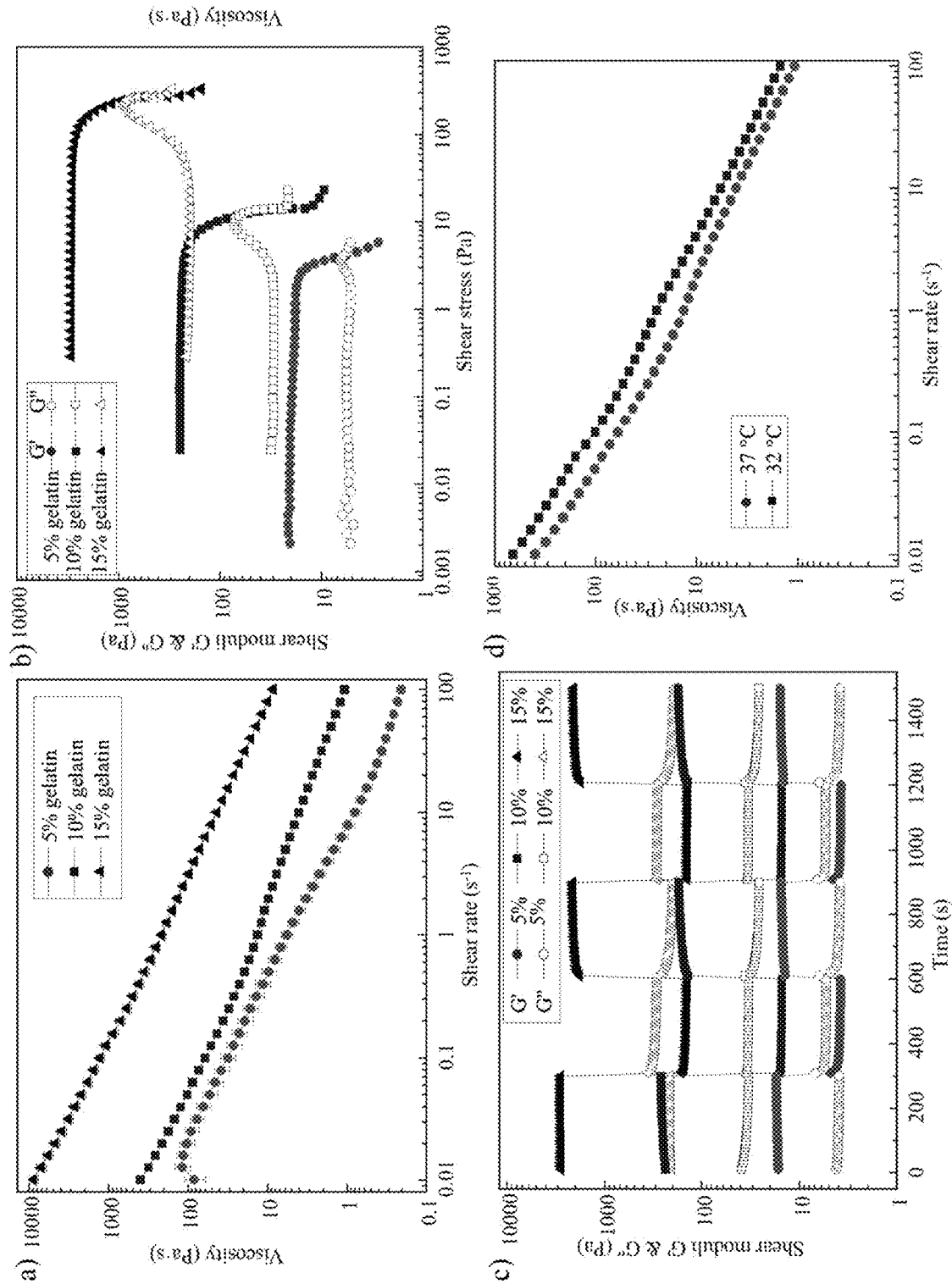
FIG. 2 illustrates examples of rheological properties measurements of the gelatin-based microgel composite ink, in accordance with various embodiments of the present disclosure.
Figure 2:
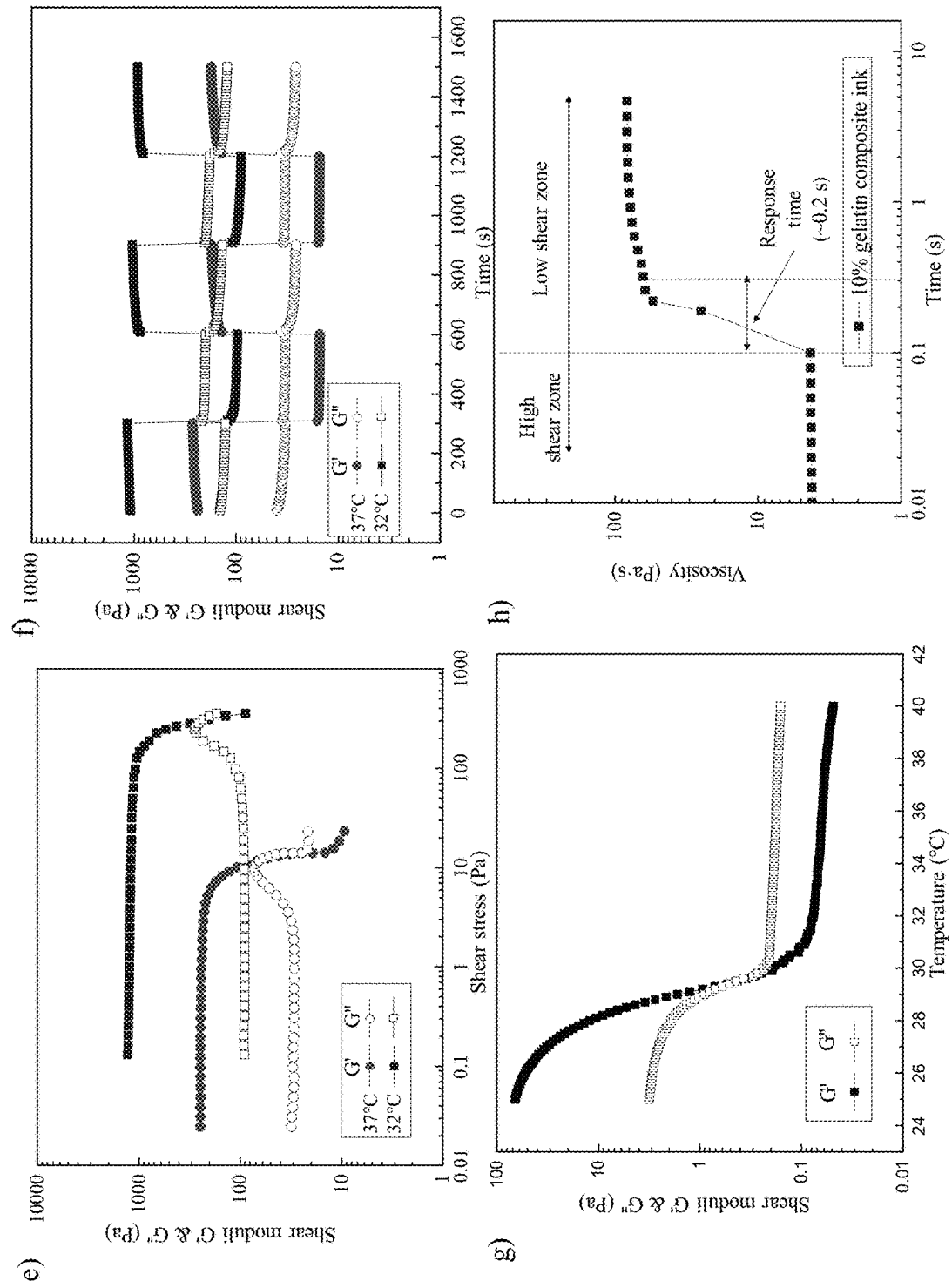

The rheological properties of the gelatin-based microgel composite ink were measured to explain the sol-gel transition behavior and the self-supporting property of the ink during the printing process. FIG. 2 illustrates examples of result plots of the rheological properties measurements: (a) decreased viscosity with increasing shear rate to show shear-thinning; (b) shear modulus as a function of shear stress of gelatin microgel-based composite ink formulations to show yield stress; (c) shear-thinning and recovery through low and high strain cycles with different gelatin microgel concentrations; (d) apparent viscosity under steady shear at different temperatures; (e) measured yield stress at different temperatures; (f) shear-thinning and self-healing through low and high strain cycles under different temperatures; (g) shear modulus at an angular frequency of 1 Hz and an oscillatory strain of 1% during cooling from 40° C. to 20° C. to show critical point; and (h) viscosity as a function of response time with transient step shear rate test.

The shear-thinning behavior of the gelatin-based microgel composite ink was measured as shown in plots (a) and (d) of FIG. 2. It was found that the viscosity of gelatin microgel suspensions with different concentrations decreases with the increase of shear rate. That is because under stressed condition, the microgels distribute along the stressed direction and present an unjammed state, resulting in the decrease of viscosity. So the ink can pass through the extrusion tip with shear-thinning phenomenon. Plots (a) and (d) of FIG. 2 also illustrate that the viscosity increases with increasing gelatin concentration and with decreasing temperature.

The yield-stress property is investigated by sweeping the shear stress and recording the shear moduli as shown in plots (b) and (e) of FIG. 2. Also seen from plots (b) and (e) of FIG. 2, when the shear stress is relatively low, the storage modulus of gelatin-based microgel composite ink is higher than its loss modulus, which demonstrates the composite ink remains jammed and presents a solid-like behavior. When the shear stress of the composite ink is higher than a critical value, the storage modulus becomes lower than the loss modulus, resulting in an unjammed state and fluid-like behavior of the composite ink so that the composite ink could be through a cannulated needle, and this critical stress value is the yield stress of the suspension. From plot (b) of FIG. 2, it can be found that with the increase of the gelatin concentration, the yield stress also increases. Temperature is another important factor for yield stress as shown in plot (e) of FIG. 2.

The reversible jamming-unjamming transition is characterized by shearing and resting for several cycles as shown in plots (c) and (f) of FIG. 2. It was found that in the resting condition, the gelatin microgels in the suspension jam together to present a solid-like behavior, while under shear the unjammed microgel particles enable the suspension to behave like a liquid. All the suspensions at different gelatin concentrations can reversibly switch the states between fluid and solid-like in a relatively short time. 11011 Plot (h) of FIG. 2 illustrates the relationship between the viscosity change and response time. The gelatin microgel-based composite ink was pre-sheared to a fully sheared state with shear rate of 100 s$^{-1}$ for 10 seconds. Then the shear rate was decreased to 1 s 1 immediately to record the viscosity change. Due to the shear-thinning effect, the viscosity of the composite ink in pre-shear rate zone is low (around 4.6 Pas), while the viscosity increases rapidly to around 80 Pas after the shear rate was decreased to 1 s$^{-1}$ in 0.2 s. This short response time indicates that the deposited ink can immediately return to solid-like behavior after being liquefied by the deposition process, thus retaining the deposited shape and forming well-defined constructs.

To print a thermoresponsive hydrogel, accurate temperature control can be used to regulate the sol-gel transition. As shown in plot (g) of FIG. 2, the 3% gelatin solution exhibits a fluid-like behavior at high temperatures, where the loss modulus is higher than the storage modulus. As the temperature drops below a critical point (e.g., approximately 30° C.), the storage modulus exceeds the storage modulus because of the formation of a physical gelatin network. The gelatin solution undergoes rapid gelation which allows the composite ink to form a gelled structure on the substrate quickly (see, e.g., FIGS. 6, 7 and 8).

Figure 3:
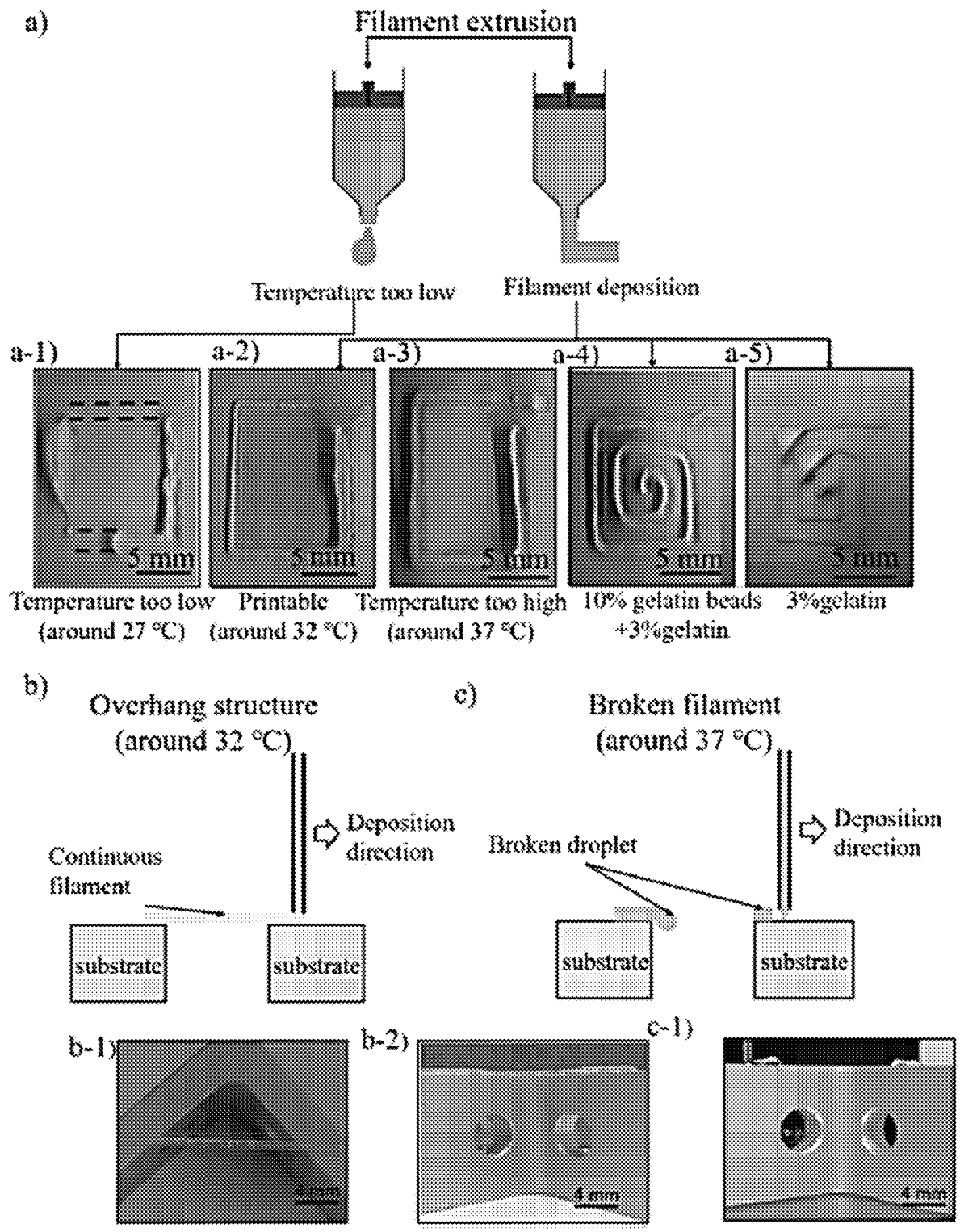
FIG. 3 illustrates temperature effects on the gelatin-based microgel composite ink, in accordance with various embodiments of the present disclosure.

Referring to FIG. 3, shown is a characterization of temperature effects on the composite ink. Square patterns were printed on paper substrates at a low temperature (below 32° C.), working temperature (around 32° C.) and high temperature (above 37° C.) to show the temperature influence on the printing process. The printing quality at a lower temperature (below 32° C.) is lower than the quality of patterns produced by printing above the critical point. It may be attributed to the fact that although the general shape of the steady shear rheology curves shown in plots (d) and (e) of FIG. 2 are similar, it shifts toward higher shear stresses and higher apparent viscosities as the temperature decreases which indicates more solid-like behavior and resistance to flow. During material extrusion and printing, this translates into intermittent clogging of the nozzle resulting in poor printing performance.

A schematic diagram illustrating the filament extrusion is shown at (a) of FIG. 3. Lines printed at a higher temperature also produce high-quality patterns although the low yield stress would limit the achievable height and complexity of printed constructs at this temperature. When extruded at a low temperature, the extrusion does not produce a continuous or consistent deposition as shown in image (a-1) of FIG. 3. Images (a-2) and (a-3) of FIG. 3 illustrate extrusion at the working temperature and at a high temperature, respectively. The gelatin microgel-based composite ink can form filaments with well-defined geometry on a receiving substrate. Filament morphology with and without gelatin microgels under the working temperature are shown in images (a-4) and (a-5) of FIG. 3, respectively.

Spanning filaments were printed to evaluate the self-supporting capability of the designed gelatin-based composite ink. A schematic diagram illustrating continuous filament deposition spanning between supporting substrates is shown at (b) of FIG. 3. Images (b-1) and (b-2) of FIG. 3 show top and front views, respectively, of the spanning filament. A schematic diagram illustrating broken droplet deposition between the supporting substrates is shown at (c) of FIG. 3. Image (e-1) of FIG. 3 is a front view of the broken droplet. When extruding beyond the substrate, the extruded composite ink switches its state from sol to gel rapidly due to physical cross-linking, which results in a relatively rigid filament that holds its shape in air. In contrast, a filament extruded at high temperature without undergoing this sol-gel transition can maintain its shape on the substrate (see, e.g., image (a-3) of FIG. 3) but not support this high tensile stress due to gravity when the filament is extended beyond the edge of the substrate. Instead, it breaks as illustrated in image (c-1) of FIG. 3.

The self-supporting ability for the composite ink to be printed overhang filament was studied by calculating the maximum shear stress $\tau_{max}$ and the maximum tensile stress $\sigma_{max}$. The filament printed between two posts in images (b-1) and (b-2) of FIG. 3 could be analyzed as a simply supported beam with a uniformly distributed weight-induced load. So the maximum shear stress which always occurs at the two end point could be calculated by:

$$\tau_{max} = \frac{F_s S_{zmax}}{I_z b} = \frac{4 F_s}{3A}$$

where $F_s$ is the maximum shear force and A is the cross-sectional area of the filament. The maximum force occurring at the two-end points is:

$$R = \frac{1}{2} qL$$

where q is the weight distribution along the beam: $p = \pi \rho g R^2$, where p is the density, g is the gravitational acceleration, R is the radius of the beam and L is the length of the beam. So that the maximum shear stress could be calculated as $$\tau_{max} = \frac{2}{3} \rho g L.$$

The maximum tensile stress which always occurs in midspan can be calculated using $$\sigma_{max} = \frac{M_{max}}{I},$$

where $M_{max}$ is the maximum bending momentum, y is the distance between the neutral axis and the analyzed surface which is equal to the radius of the filament (R) herein, and I is the moment of inertia. The maximum bending moment is:

$$M_{max} = \frac{1}{8} qL^2$$

and the moment of inertia is:

$$I = \frac{1}{4} \pi R^4,$$

so the maximum tensile stress can be rewritten as:

$$\sigma_{max} = \frac{\rho g L^2}{2R}.$$

To estimate whether an overhanging filament could be printed between two posts, the calculated maximum shear stress and maximum tensile stress were compared with the shear stress $\tau_{ink}$ and tensile stress $\sigma_{max}$ of the designed gelatin microgel-based composite ink. Based on the shear stress of composite ink at 31° C., which was measured using rheology as shown in FIG. 2, graph (2) to be 251.5 Pa, the tensile stress of the composite ink can be estimated by $$\sigma_{ink} = \frac{3}{\sqrt{2}} \tau_{ink}$$

according to the octahedral shear stress theory, resulting in a tensile stress value of 533.46 Pa. The $\tau_{max}$ and $\sigma_{max}$ of the overhang beam are 65.5 Pa and 306.3 Pa, respectively, which are lower than the value of $\tau_{ink}$ and $\sigma_{ink}$, so the filament does not break up during deposition.

Figure 4:
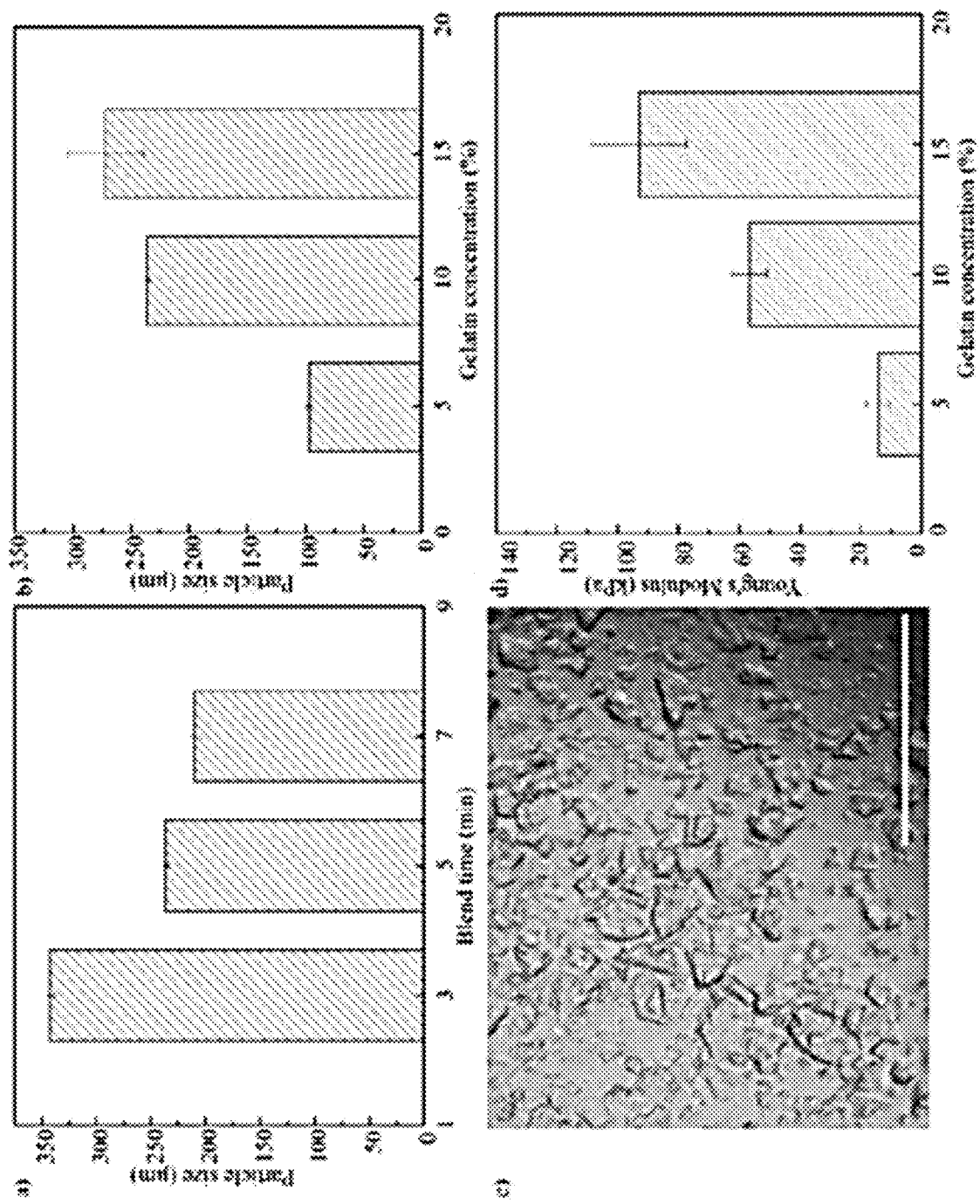
FIG. 4 illustrates examples of particle size and mechanical characterization of the microgel-based composite ink, in accordance with various embodiments of the present disclosure.
Figure 4:
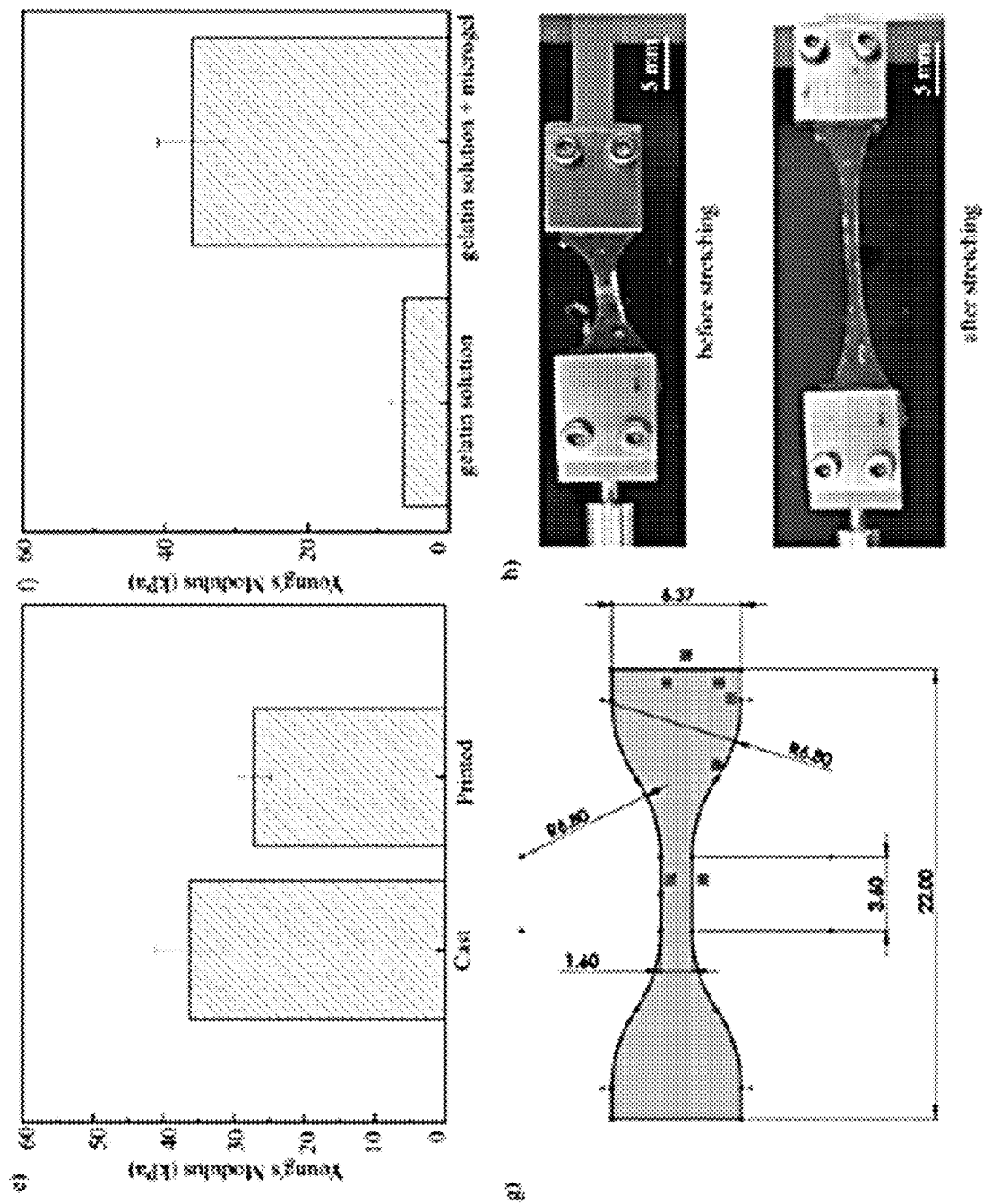

The gelatin microgels can also improve the printing fidelity as shown in images (a-4) and (a-5) of FIG. 3. The printed line morphology is strongly dependent on the gelatin microgel size. The finer the gelatin microgel, the better the printed line morphology. FIG. 4 illustrates examples of particle size and mechanical characterization of the microgel-based composite ink. Graphs (a) and (b) of FIG. 4 depict the gelatin microgel particle size as a function of (a) blend time and (b) gelatin concentration. Image (c) of FIG. 4 shows the optical micrograph of gelatin microgels in excess water (scale bar: 1 mm). Graph (d) of FIG. 4 illustrates the Young's modulus of the gelatin microgel-based composite ink at different concentrations based on tensile tests. Graph (e) of FIG. 4 illustrates the Young's modulus of cast and printed 10% gelatin microgel-based composite ink. Graph (f) of FIG. 4 shows the Young's modulus of gelatin microgel-based composite ink (3% gelatin solution and 10% gelatin microgel) and gelatin solution (3% gelatin) with different concentration. The diagram (g) of FIG. 4 depicts the designed dog bone-shaped specimen dimensions. The images (h) of FIG. 4 show a gelatin-based specimen without elongation and with 20 mm elongation (scale bar: 5 mm).

The average size of the gelatin microgels can be controlled by varying either the gelatin concentration or blend time as shown in graphs (a) and (b) of FIG. 4, respectively. From graph (b) of FIG. 4, it can be found that the average microgel diameter increases with the increase of the gelatin concentration using the same blend time. In contrast, the microgel size decreases with the increasing blend time and will reach a plateau region as shown in graph (a) of FIG. 4. A time of 5 minutes was chosen as the blending time in this examination for material preparation and 3D structure printing since extending the blend time has little impact on the microgel size.

To ensure the mechanical stiffness of the printed structures, TG can be added into the gelatin-based microgel composite ink to cause the further chemical cross-linking of gelatin solution after the rapid physical cross-linking of gelatin solution caused by the decrease of ambient temperature. The mechanical properties of the chemically cross-linked gelatin-based microgel composite ink were investigated using tensile tests. The samples were prepared through printing in the air and casting in the designed mold with the same disclosed dog-bone structure as shown in diagram (g) of FIG. 4. During stretching, the stress of the materials with 5%, 10%, and 15% gelatin microgels mixed with 3% gelatin increased linearly with the strain in the elastic region.

Under additional strain, the cross-linked gelatin microgel composite undergoes plastic deformation and the stress increases significantly. The Young's moduli of the gelatin microgel suspensions at different concentrations were measured based on slopes of the stress-strain curves at linear regions, which were around 14.4 kPa, 36.3 kPa, and 56.8 kPa, respectively. It was found that with the increase of microgel gelatin concentration, the Young's modulus also increased as shown in graph (d) of FIG. 4. The addition of gelatin microgels to the gelatin solution also enhanced the Young's moduli as illustrated in graph (f) of FIG. 4, where the Young's Modulus of cross-linked 3% gelatin is 6.4 kPa without added gelatin microgels and is 36.3 kPa with the addition of 10% gelatin microgels. The average Young's modulus of the printed specimens was a little lower (27.1 kPa) than the casting parts (36.3 kPa) while almost in the same magnitude which demonstrate the good mechanical properties of the structures printed by the designed gelatin composite ink (graph (e) of FIG. 4).

The Young's modulus of the designed gelatin microgel-based composite ink was lower compared with other gelatin-based material for tissue engineering such as GeIMA (43.0 kPa for 10%), GGMA and GeIMA double-network hydrogel (80.0 kPa for 0.5% GGMA hydrogels and 20% GeIMA) and GMAC (2.8 MPa for GMAC31 and to 4.6 MPa for GMAC11 and GMAC13). This low Young's modulus makes structures fabricated using the designed composite ink more flexible and easier to handle for tissue engineering applications such as transplantation work. Images (h) of FIG. 4 also illustrates the elasticity of the designed composite ink, showing that the dog bone-shaped specimen could be elongated up to 20 mm without any breakage.

Injectability and Printability

For injectable materials, injectability (the capability for those hydrogel-based materials to be homogeneously extruded through a syringe-cannulated needle combination) is an important property for its use in tissue engineering applications such as minimally invasive surgery. The injectability is always related to the viscosity of the material and may be evaluated based on the force or pressure needed to induce flow of the materials through needle. Needle length, needle inner diameter and needle opening shape can also affect these measurements. According to the force needed for injection, the materials can be rated as very easy to inject (injection force: 0 N-10 N), easy to inject (injection force: 11 N-25 N), injectable (injection force: 26 N-100 N), difficult to inject (injection force: 100 N-130 N) and very difficult to inject (inject force: >130 N). The injection force f can be determined based on the Hagen-Poiseuille Equation:

$$f = \frac{32 \mu L Q D_s^2}{d^4} \quad (3)$$

where $\mu$ is the viscosity (1 Pas), L is the needle length (12.7 mm), Q is the volumetric flow rate (0.3362 mm³/s), d is the nozzle inner diameter (0.41 mm), and Ds is the inner diameter of the syringe barrel (12 mm). As such, the injection force is calculated as 17.4 N, and the gelatin microgel-based composite ink is easy to inject.

The disclosed injectable hydrogel-based composite ink benefits from its shear-thinning and self-supporting properties, which enable printing of complex and overhang structures directly in the air. Printability is an important property for the composite ink to fabricate 3D structures. The printability here was mainly evaluated by the morphology and dimensions of the deposited filaments. Since a single extruded filament is the most basic unit for fabrication of a complicated 3D structures, the evaluation of the printing conditions' effect on the extruded filaments is the first step before 3D structure implementation. All of the extruded filaments were printed on glass slides for investigation and filament width was the evaluation criteria since the structure's resolution depends on the filament width. The filament width was measured using images captured with a microscope.

Figure 5:
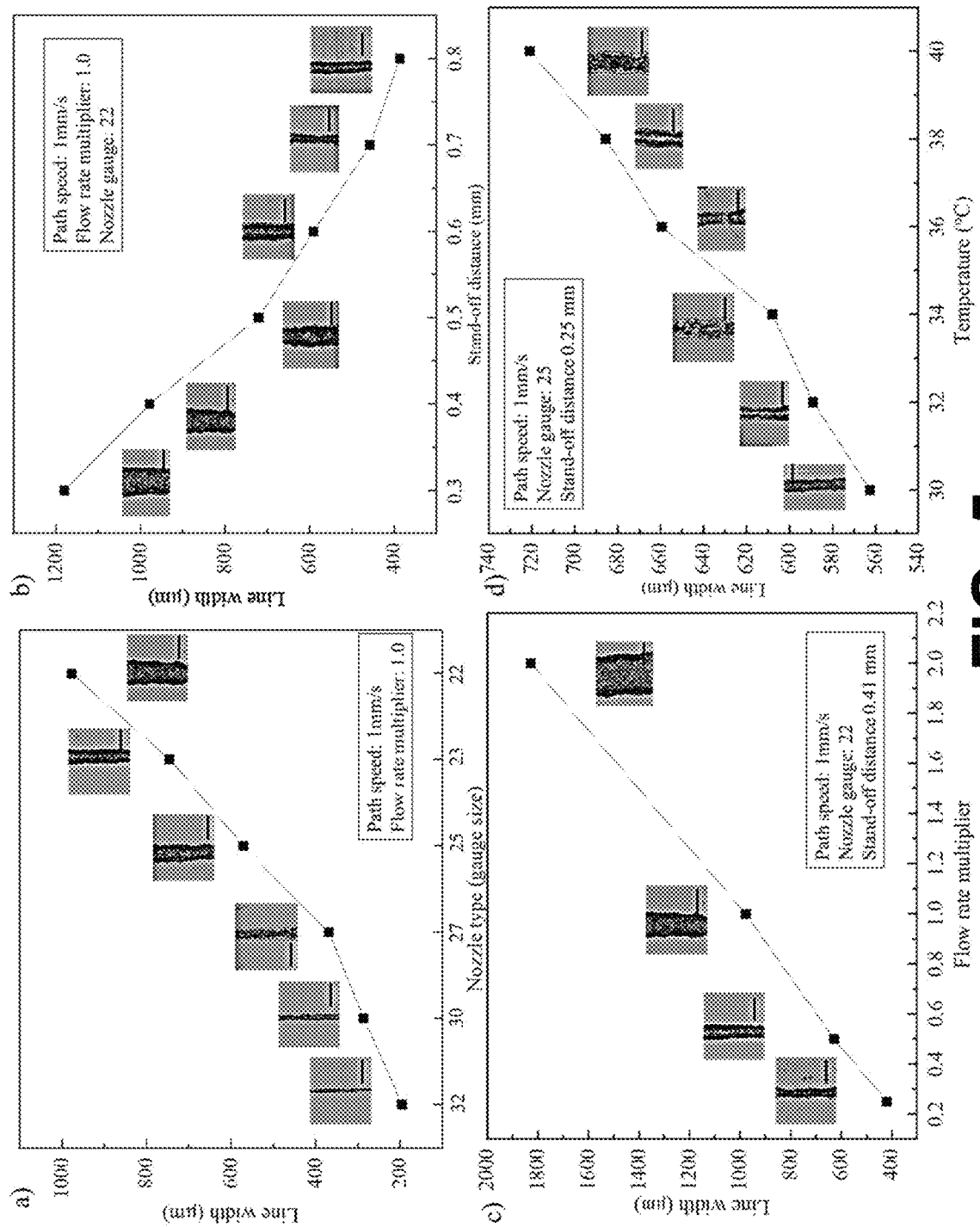
FIG. 5 illustrates a printability analysis of the operating conditions on the filament width, in accordance with various embodiments of the present disclosure.

As the gelatin-gelatin composite ink was directly printed in the air, the printability was assessed in relation to four operating conditions: nozzle type, standoff distance, material flow rate, and printing temperature. FIG. 5 illustrates the printability analysis of the operating conditions on the filament width. Plot (a) of FIG. 5 shows the width of the achievable deposited filaments as a function of nozzle type with some representative filaments printed by each nozzle. Plot (b) of FIG. 5 shows the filament width as a function of standoff distance. Plot (c) of FIG. 5 shows the filament width as a function of material flow rate multiplier. Plot (d) of FIG. 5 shows the filament width as a function of operating temperature. (Scale bars=1,000 µm).

The dispensing tip, or nozzle, is the most basic component for extrusion-based 3D printing, so the effect of the nozzle type on the filament width was firstly investigated. The printing path speed was set as 1.0 mm/second, the material flow rate as 1.0 and the standoff distances were set to be the same as the nozzle diameter to control the experiment variables. It can be seen from plot (a) of FIG. 5 that the filament width can be adjusted by changing the nozzle type (in terms of diameter: 100 µm for Gauge 32 nozzle, 150 µm for Gauge 30 nozzle, 200 µm for Gauge 27 nozzle, 250 µm for Gauge 25 nozzle, 330 µm for Gauge 23 nozzle, and 400 µm for Gauge 22 nozzle). The bigger the nozzle diameter, the wider the filament width. The filaments are relatively smooth and have no obvious irregular boundaries which may be attributed to the sol-gel transition of the composite matrix material, as illustrated in FIG. 5 and discussed above.

Standoff distance is the distance between the dispensing tip and the receiving substrate. For structure printing, the receiving substrate also includes the surface of the previously printed layers. In this part, a nozzle gauge of 22 (inner diameter of 0.41 mm) was chosen, the printing path speed was set to 1.0 mm/second and the material flow rate was set at 1.0. The only variable was the standoff distance. As illustrated in plot (b) of FIG. 5, the filament diameter will change according to the standoff distance. When the standoff distance is smaller than the height of the printed filament, the nozzle tip will compress the deposited filament and make the filament significantly wider. By increasing the standoff distance, the gravity force and dragging effect will affect the already printed filament, so the filament width will decrease accordingly. When the standoff distance exceeds a critical value, the printed filament will break up to droplets due to the force of gravity and dragging effect.

Since the machine used in this experiment was a ball screw-based 3D printer, the material flow rate was calculated based on the pre-set parameters: nozzle type, layer thickness (standoff distance), printing path speed, pulse per nanoliter and material flow rate multiplier. The function where path width times path height defines the cross-section can be calculated. The cross-section times print speed gives volume per unit time to be dispensed. The volume per unit time times pulse per nanoliter gives how fast in pulses per second to dispense. At last, the result above is multiplied by the material flow rate multiplier can be used to modify the final material flow rate to account for over or under sized filament. Here a nozzle with gauge of 22 (inner diameter of 0.41 mm) was chosen, standoff distance was set as 0.41 mm and printing path speed was set as 1 mm/second to control the variables. The filament width decreases with the decreases of the material flow rate multiplier as shown in plot (c) of FIG. 5.

As aforementioned gelatin is a thermo-sensitive hydrogel, the temperature influence on the filament morphology was also investigated to determine the optimal printing conditions. The nozzle gauge was changed to 25 (inner diameter of 0.25 mm) herein since the higher temperature results in a wider line width, which exceeds the available field of view for microscopic imaging. Other parameters were set accordingly: standoff distance was 0.25 mm, printing path speed was 1 mm/second and flow rate was 1.0. An almost linear relationship between the temperature and the filament width could be found as shown in plot (d) of FIG. 5.

Printing Results

Lattice Printing

Figure 6:
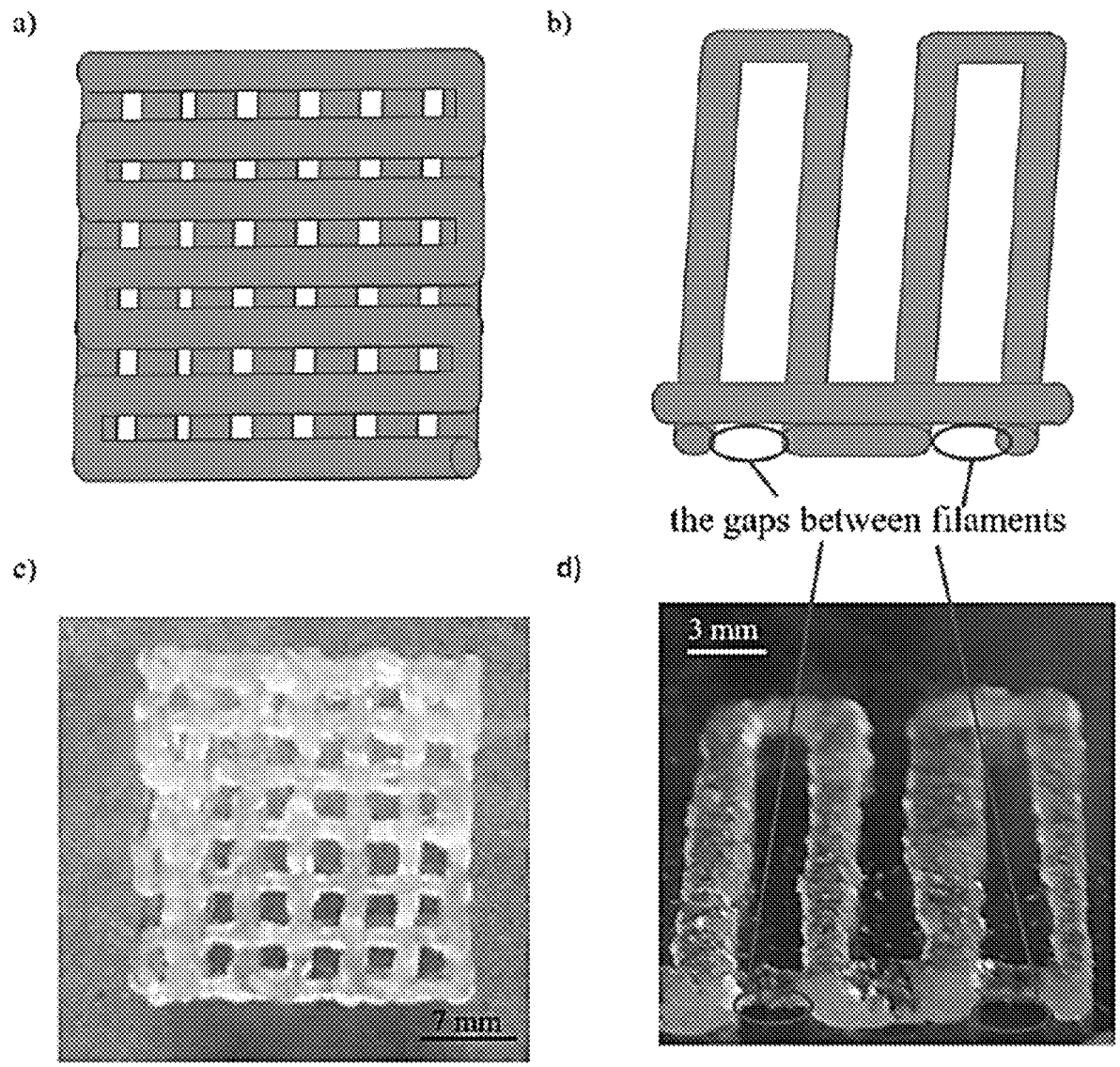
FIG. 6 illustrates an example of a lattice structure formed using the gelatin-based microgel composite ink, in accordance with various embodiments of the present disclosure.

Since the gelatin-based microgel composite ink is used to provide a synthetic substitute ECM as a scaffold material, here a multilayered lattice structure was printed since the lattice structure can introduce large and interconnected pores for enhanced porosity can enhance nutrient transport and waste removal by decreasing diffusion distance. FIG. 6 illustrates an example of a lattice structure. Schematic diagram (a) of FIG. 6 is a top view of a complete structure and schematic diagram (b) of FIG. 6 is an isotropic view of the first two layers of lattice structure printing. Image (c) of FIG. 6 is a top view of a completed structure and image (d) of FIG. 6 is a side view of the first two layers.

Depicted in (a) and (b) of FIG. 6 is the schematic for printing a complete lattice structure and the first two layers of the lattice structure. The 21 mm×21 mm lattice structure with 7 lines per layer could be formed up to 8 layers thick with a height of 5.6 mm. Each layer includes a set of parallel filaments which are perpendicular to the adjacent layers. Gaps between adjacent filaments are clearly visible in the XY plane as illustrated in image (c) of FIG. 6. In the Z direction, the gaps between filaments in different layers are still obvious. For better illustration of the gaps between filaments, a two-layer lattice structure shown in image (d) of FIG. 6 was printed.

Tube and Cup Printing

Figure 7:
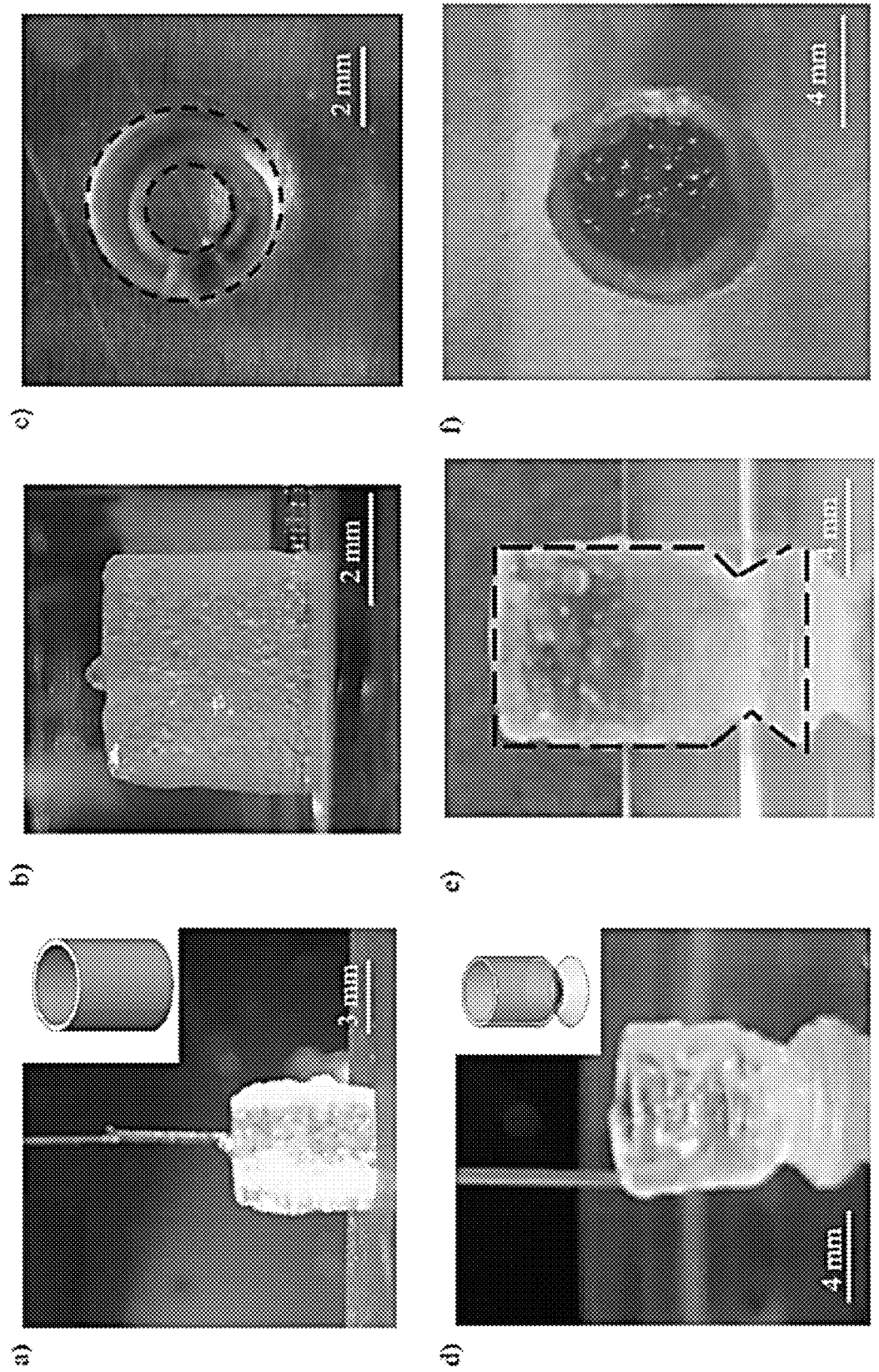
FIG. 7 illustrates examples of tubular and cup-shaped structures printed with the gelatin-based microgel composite ink, in accordance with various embodiments of the present disclosure.

More complex 3D structures were also printed to show the robustness of the disclosed composite ink. For example, FIG. 7 illustrates tubular and cup-shaped structures, as shown, respectively, in the insets of images (a) and (d) of FIG. 7. A straight tube was printed to show that the composite ink could be directly printed in the air. The tube had a designed height of 6 mm and outer diameter of 5 mm, the wall thickness of the tube is 0.4 mm. Image (a) of FIG. 7 shows the tube-shaped structure while under printing (with the inset showing the schematic used for tube-shaped structure printing). The side view and top view of images (b) and (c) of FIG. 7 show the finished tube structure. The surface of the tube was very smooth, and the structure was vertical without any angle of inclination, as shown in the images of FIG. 7.

A cup-shaped construct was also printed to show the ability to form 3D enclosed objects with thin walls. The cup-shaped construct had a height of 12 mm and outer diameter of 8 mm, the overhang inclination angle was 45°. Image (d) of FIG. 7 shows the cup-shaped structure while under printing (with the inset showing the schematic used for cup-shaped structure printing). The front view and top view of images (e) and (f) of FIG. 7 show the finished cup-shaped structure. (Scale bars=3 mm for image (a) of FIG. 7, 2 mm for images (b) and (c) of FIGS. 7, and 4 mm for images (d), (e) and (f) of FIG. 7). Some deformation of the printed structure was observed as the upper layers were printed, but the ink was elastic enough to revert to the original printed shape once the nozzle traveled away. The printed cup exhibited a high print fidelity as shown in the images. Some red colored food dye was added into the deionized water to improve the visibility. There was no leaking observed after the cup was filled with deionized water (images (e) and (I) of FIG. 7), which means that all deposited layers are connected together seamlessly.

Overhang Structure Printing

Figure 8:
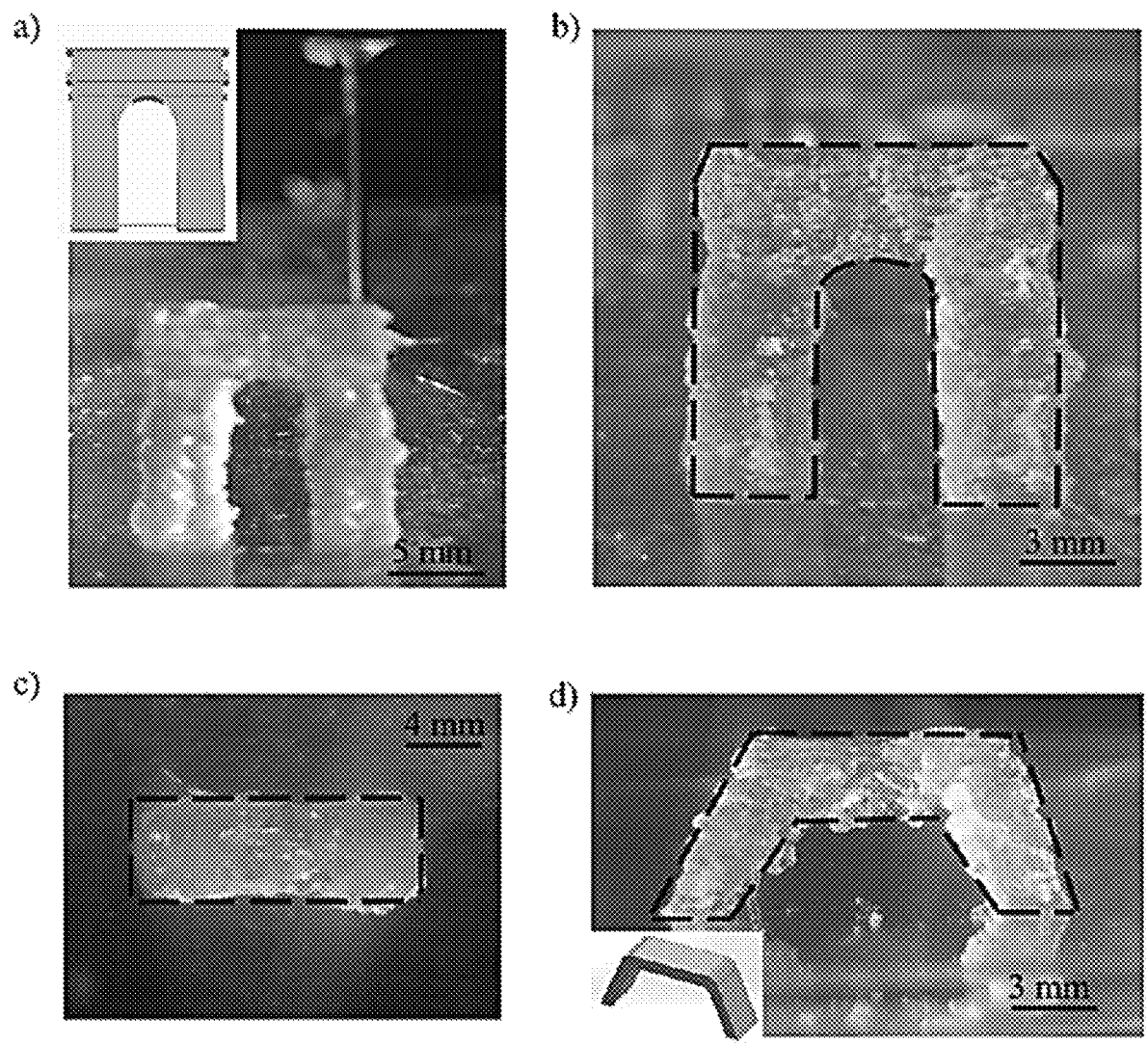
FIG. 8 illustrates examples of overhang structures printed with the gelatin-based microgel composite ink, in accordance with various embodiments of the present disclosure.

To further show the self-supporting capability of the gelatin-based microgel composite ink, some overhang structures were printed. FIG. 8 illustrates examples of the overhang structures printed with the composite ink. Image (a) of FIG. 8 shows a designed Triumphal Arch during printing (with the inset showing the schematic of the designed Triumphal Arch). The simplified triumphal arch with a height of 14 mm and spanning length (width of the gap in the middle) of 10 mm. The post of the Triumphal Arch is vertical without any inclination angle. Image (b) of FIG. 8 shows the front view of the finished Triumphal Arch. Scale bars=5 mm for image (a) of FIG. 8 and 4 mm for image (b) of FIG. 8. A designed bridge structure with a width of 4 mm, height of 7.5 mm, and a spanning length of 10 mm was also fabricated. The overhang inclination angle was 67°. Images (c) and (d) of FIG. 8 are, respectively, top and front views of the finished bridge structure (with the inset in image (d) of FIG. 8 showing the schematic of the designed bridge structure). Scale bars=4 mm for image (c) of FIG. 8 and 3 mm for image (d) of FIG. 8. The shape of the bridge is well defined after printing as shown in the images. The overhang between two posts of the Arch during printing and after printing and the bridge floor were both very flat without any deflection which confirms the self-supporting capability of the composite ink.

Printing Fidelity Analysis

Figure 9:
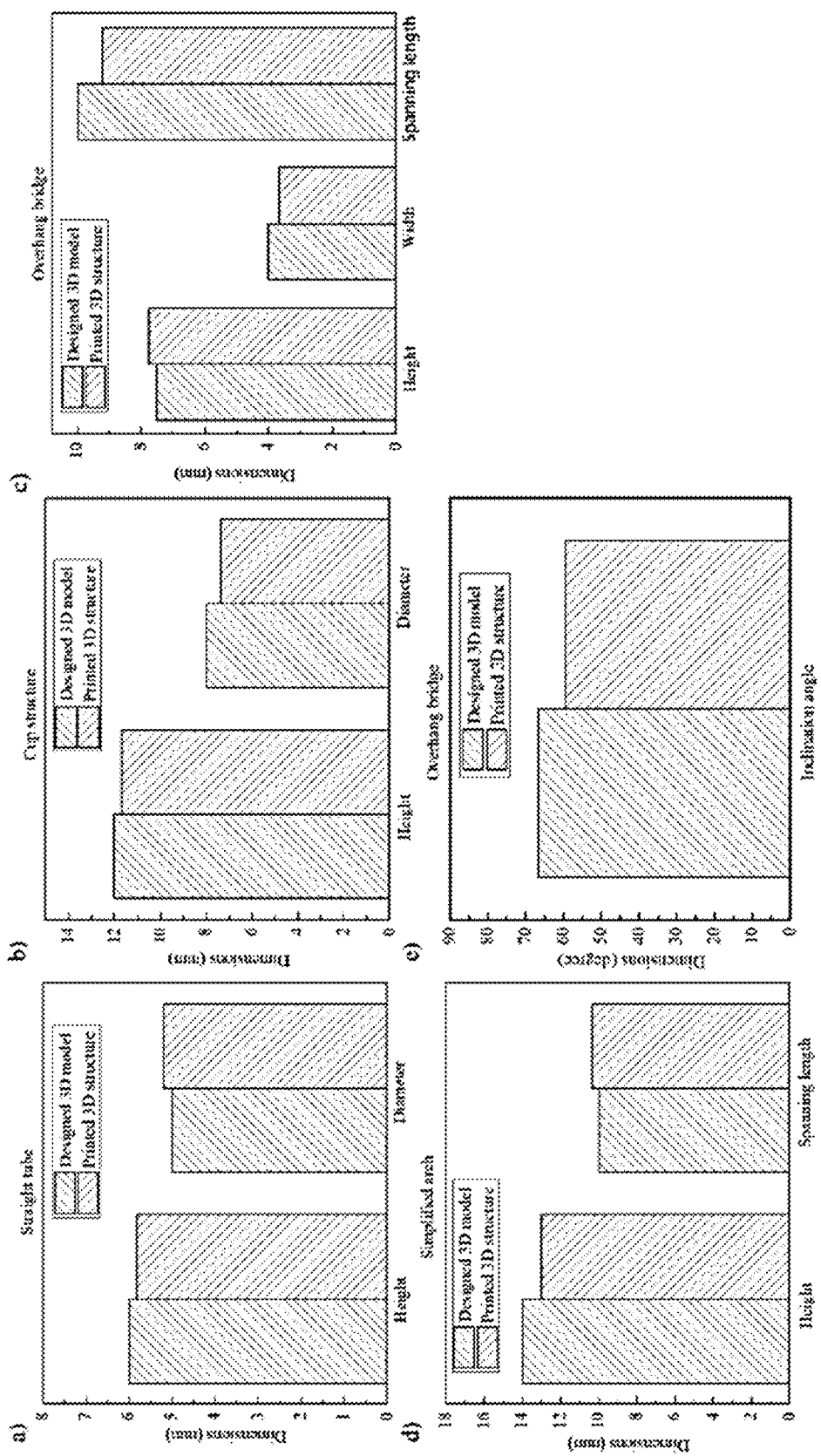
FIG. 9 illustrates a comparison of dimensions between designed 3D model and printed 3D structures of FIGS. 6-8, in accordance with various embodiments of the present disclosure.

To assess the print fidelity of the designed gelatin-based microgel composite ink, the geometries of the printed complex 3D structures: straight tube, cup structure, bridge structure (without a post) and the simplified Triumphal Arch were measured and compared with the designed 3D models. FIG. 9 illustrates the comparison of dimensions between designed 3D model and printed 3D structures for: (a) the straight tube, (b) the cup structure, (c) the Triumphal Arch, (d) and (e) the bridge structure. The overall dimensions including the diameter, height, inclination angle, length and width of the designed 3D model and the printed 3D structure are compared accordingly in FIG. 9. Slight differences were allowed since the printed structure is soft and flexible, and at least a portion of the dimensional variability may come from the deformation during the measurement process. No significant deformation was observed between the designed model and the printed 3D structure which confirms that the gelatin-based microgel composite ink can effectively hold the complex structure as a self-supporting material.

Applications to Bioprinting

Assessment of Volume Shrinkage and Water Content of Composite Ink

Figure 10:
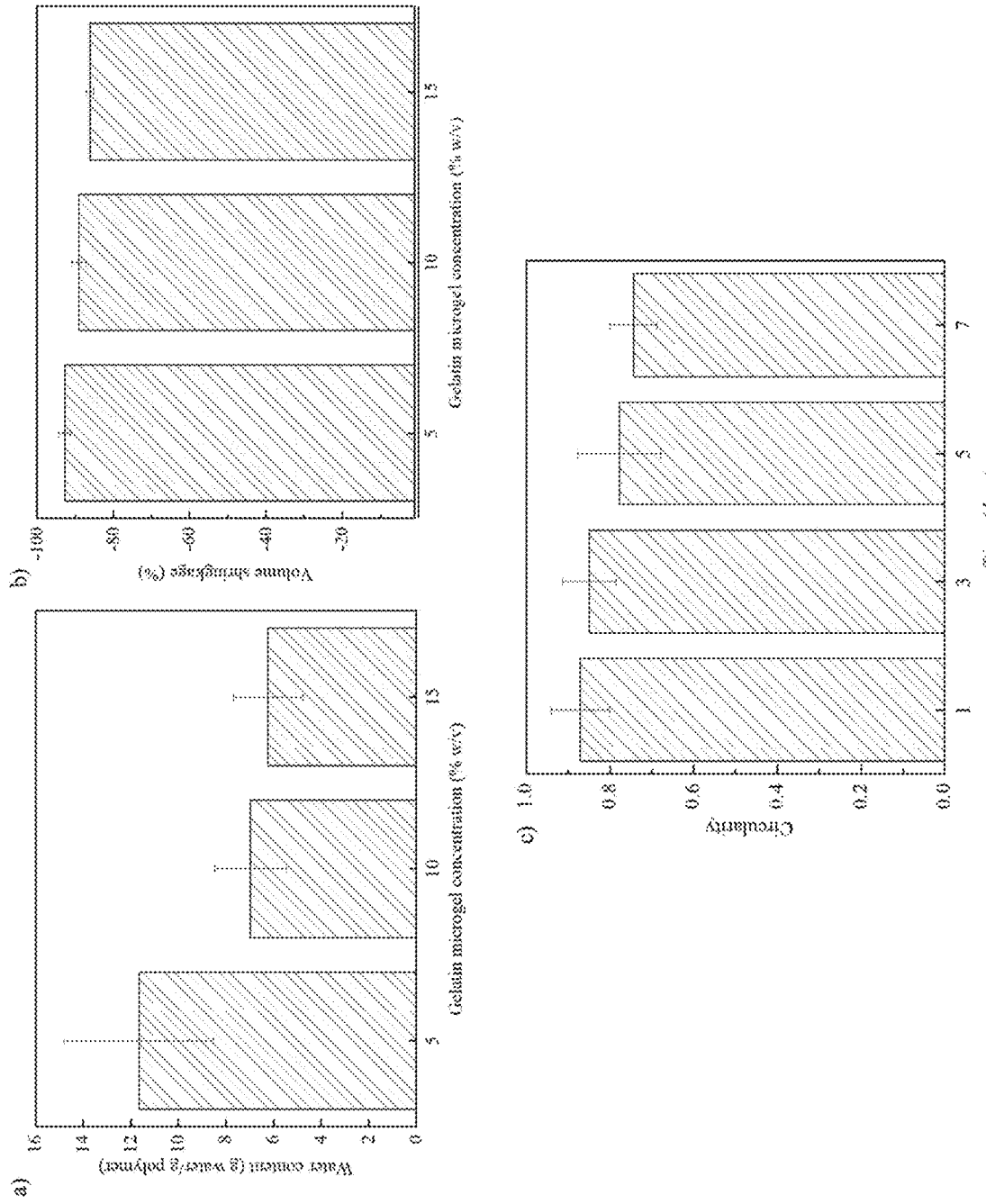
FIG. 10 illustrates examples of biological properties for the designed composite ink, in accordance with various embodiments of the present disclosure.
Figure 10:
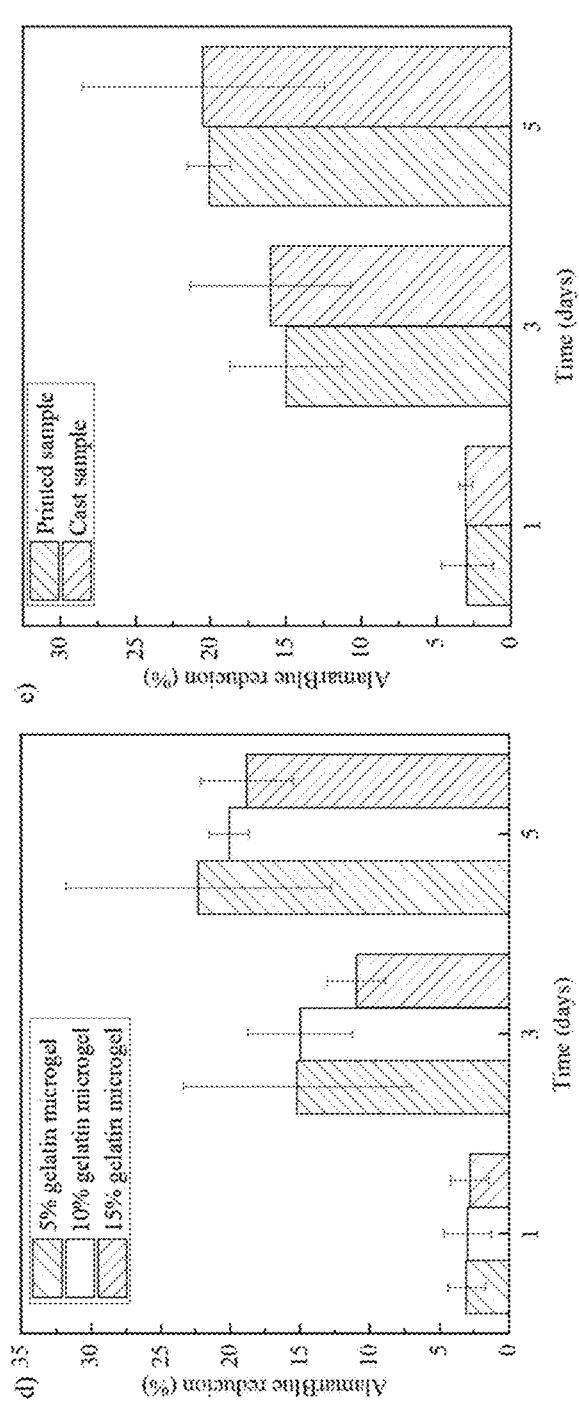
Figure 10:
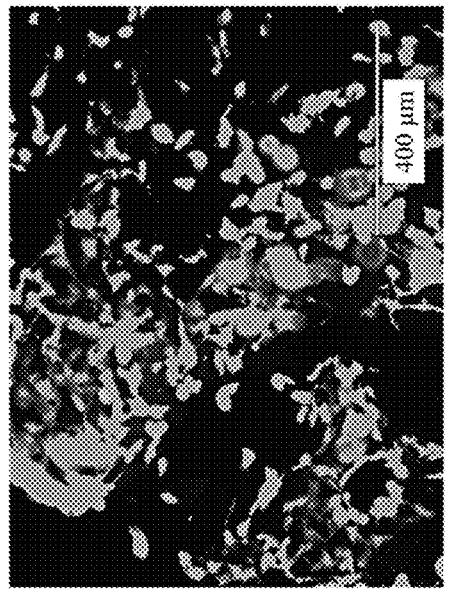
Figure 10:
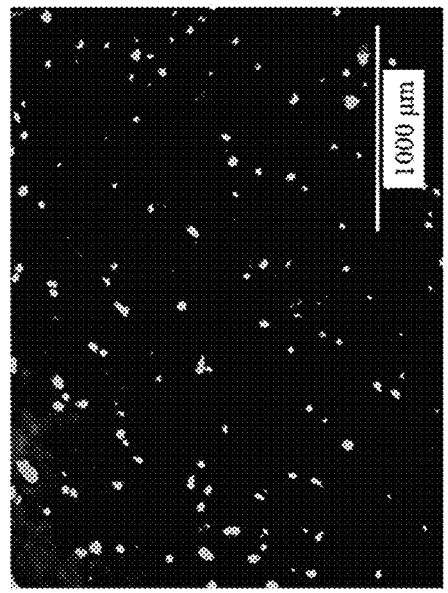

Hydrogels are hydrophilic polymer networks, which may absorb, at an equilibrium swelling level, up to hundreds of times their dry weight in water. Hence, the value of water content in a hydrogel can be viewed as an index to determine the efficiency of transport of nutrients into and waste out of the gel. FIG. 10 illustrates examples of biological properties for the designed composite ink including graphs of water content (a) and volume shrinkage (b) of the composite ink with different gelatin concentrations for microgels. Graph (c) of FIG. 10 shows the relationship between cell circularity and culture time. Graph (d) of FIG. 10 illustrates the AlamarBlue reduction percentage differences between printed sample and cast sample. Graph (e) of FIG. 10 shows the AlamarBlue reduction percentage differences with different gelatin concentrations for microgels. Cell morphology after being cultured for 0 days and 14 days are shown in images (1) and (g) of FIG. 10. Scale bars=1,000 μm for image (f) of FIG. 10, 400 μm for image (g) of FIG. 10.

The water content of each material with different gelatin microgel concentrations is shown in graph (a) of FIG. 10. It was found that higher concentration gelatin microgel will lead to less water content (11.66 g/g for 5% gelatin microgel, 6.96 g/g for 10% gelatin microgel and 6.23 g/g for 15% gelatin microgel). All of the designed gelatin microgel-based composite inks exhibited a higher water content than other reported injectable composite hydrogels such as PNIPAM-COOH (1.25 g/g for 10%), PEG-PLGA-PEG (1.5 g/g) and Poly(NIPAAm-co-HEMA-co-MAPLA) (0.87 g/g). High water content composite ink has advantages for tissue regeneration because of their permeability for oxygen, nutrients, and other water-soluble metabolites.

To assess the structural stability as well as the volume stability of the composite hydrogels and to mimic the conditions of a physiological environment, the volume shrinkage of various hydrogels after gel formation was also compared. As shown in graph (b) of FIG. 10, the higher concentration of gelatin microgels can decrease the degree of volume shrinkage (−92.67% for 5% of gelatin microgel, −88.99% for 10% gelatin microgel, and −86.05% for 15% gelatin microgel). From a tissue engineering perspective, scaffolds featured with enormous volume collapses may represent several drawbacks, such as squeezing the cells out of the scaffold, and/or damaging the cells. So the addition of gelatin microgels can significantly improve the volume stability and support a better physiological environment.

Evaluation of Biocompatibility

The gelatin-based microgel composite can provide a support structure for cells to fabricate or regenerate tissues. NIH 3T3 mouse fibroblasts were cultured in the gelatin-based microgel composite ink to evaluate the feasibility of this designed material for 3D cell culture and the effect of the printing in air process on the encapsulated cells.

To study the cell viability and morphology, straight tube structures with a wall thickness of 0.4 mm were directly printed in the air. The prepared cell ink was extruded with a nozzle temperature of 32° C. to achieve optimal printing performance. After printing the structure was put into a 37° C. incubator for covalent cross-linking to form physiologically stable constructs since TG was pre-mixed with the composite ink. Then the cross-linked structure was immersed in culture media and cultured in a $CO_2$ incubator. Images (f) and (g) of FIG. 10 demonstrate that the cells survived well in the printed structures after printing (0 days) and 14 days of static incubation.

Circularity of living cells were calculated to quantitatively assess the morphology difference of cells which were cultured after 1, 3, 5, and 7 days, respectively. Circularity ($4\pi \times area/perimeter^2$) describes the roundness of a cell and ranges from 0 to 1, with 1 denoting cells with a perfectly circular shape. Generally, the calculated circularity of observed cells is distributed between two regimes: 1) rounded with high circularity which indicates low cell spreading, and 2) elongated with low circularity which indicates extensive spreading. Average circularity data for cells cultured for each period are presented in graph (c) of FIG. 10. The circularity of living cells decreases over time which indicates cell-scaffold interactions analogous to those found in native ECM.

In addition, AlamarBlue reduction testing was conducted on printed and cast cell-laden gelatin-based microgel composite ink specimens of different concentrations to quantify the metabolic activity of the cultured cells after 1, 3, and 5 days. The AlamarBlue reduction indexes of different gelatin microgel concentrations are investigated as shown in graph (d) of FIG. 10. The lower concentration gelatin microgels will lead to good metabolic activity for cells since the polymer chains inhibit diffusion through the hydrogel and a lower polymer concentration makes it better to supply nutrients and remove waste from cells throughout the bulk construct than higher polymer concentration counterparts. As seen from graph (e) of FIG. 10, the cells within the printed samples and cast samples have similar metabolic activity and the AlamarBlue reduction index increases over time which indicates the suitability of the disclosed gelatin-based microgel composite ink directly printing in air approach.

Microgel-based 3D bioprinting ink design is a valuable tool for improving the printability of desirable build materials without having to include non-ideal components in the overall formulation. This concept has been demonstrated herein using gelatin as a model biomaterial which has a non-ideal printing behavior. By preprocessing the gelatin into covalently cross-linked microgels, a fully biocompatible rheology modifier is obtained. In combination with a curable gelatin phase, the gelatin microgels enable convenient fabrication of constructs from only gelatin, without the need for any other polymeric or inorganic materials to facilitate the fabrication process. In addition to reducing the ink formulation complexity, this approach may facilitate translation of 3D bioprinted constructs to clinical applications because gelatin has been approved by regulatory agencies for clinical use in other devices.

The microgel-based composite ink comprises a microgel solid phase and a cross-linkable solution phase. For validation, the solid phase in presented in this disclosure is a gelled gelatin microgel, and the continuous phase is gelatin solution-based acellular or cellular suspension. The composite ink can be injected or printed directly in air with a physical cross-linking process to hold the structure at room temperature due to its yield-stress property. The fabricated part can have a further chemical cross-linking process by immersing it in a transglutaminase solution to enzymatically gel the enclosed gelatin solution, making a cellular construct. Gelatin hydrogel was chosen as the example used for the microgel material herein since packed gelatin microgels are as cell-responsive as gelatin itself and also enhance the effective viscosity and yield stress behavior of the resulting ink. As such, well-defined constructs can be fabricated using the proposed injectable hydrogel composite ink.

From the foregoing, it will be seen that aspects herein are well adapted to attain all the ends and objects hereinabove set forth together with other advantages which are obvious and which are inherent to the structure.

It will be understood that certain features and sub-combinations are of utility and may be employed without reference to other features and sub-combinations. This is contemplated by and is within the scope of the claims.

Since many possible aspects may be made without departing from the scope thereof, it is to be understood that all matter herein set forth or shown in the accompanying drawings is to be interpreted as illustrative and not in a limiting sense.

Various modifications and variations can be made to the compounds, compositions and methods described herein. Other aspects of the compounds, compositions and methods described herein will be apparent from consideration of the specification and practice of the compounds, compositions and methods disclosed herein. It is intended that the specification and examples be considered as exemplary.

Therefore, at least the following is claimed:

1. An injectable composite ink comprising:
   a hydrogel continuous phase; and
   a plurality of gelatin-containing microgels comprising a hydrogel, the plurality of gelatin-containing microgels comprising the hydrogel being dispersed within the hydrogel continuous phase,
   wherein the gelatin-containing microgels comprise gelatin having a bloom strength of between about 200 and about 300,
   wherein a concentration of the gelatin in the gelatin-containing microgels is 5% w/v, 10% w/v, or 15% w/v,
   wherein hydrogel continuous phase is between about 1 wt % to about 10 wt % of the injectable composite ink,
   wherein the gelatin-containing microgels is between about 90 wt % to about 99 wt % of the injectable composite ink, and
   wherein the injectable composite ink has a measurable Young's modulus of between 14.4 kPa and 56.8 kPa.

2. The injectable composite ink of claim 1, wherein the hydrogel continuous phase comprises a different hydrogel than the hydrogel of the gelatin-containing microgels.

3. The injectable composite ink of claim 2, wherein the hydrogel continuous phase comprises a hydrogel dispersed within the hydrogel continuous phase, wherein the hydrogel comprises one or more of: chitosan, collagen, alginate, hyaluronic acid (HA), heparin, chondroitin sulfate, poly (ethylene glycol) (PEG), or poly (vinyl alcohol) (PVA).

4. The injectable composite ink of claim 1, wherein the hydrogel continuous phase comprises gelatin.

5. The injectable composite ink of claim 4, wherein the gelatin has an average molecular weight of between about 50,000 Da to about 100,000 Da.

6. The injectable composite ink of claim 1, wherein the plurality of gelatin-containing microgels have an average particle size of between about 100 μm and about 500 μm.

7. The injectable composite ink of claim 1, wherein the gelatin in the plurality of gelatin-containing microgels is cross-linked.

8. The injectable composite ink of claim 1, wherein the hydrogel continuous phase comprises gelatin in an amount of between about 1 wt % to about 10 wt % of the injectable composite ink.

9. The injectable composite ink of claim 1, wherein the injectable composite ink further comprises a cross-linking agent.

10. The injectable composite ink of claim 9, wherein a concentration of the cross-linking agent in the injectable composite ink is between about 0.1% w/v and about 5% w/v transglutaminase.

11. The injectable composite ink of claim 1, wherein the hydrogel continuous phase and gelatin-containing microgels are covalently cross-linked with one another.

12. The injectable composite ink of claim 1, wherein the injectable composite ink has an injection force of between 0 N and about 25 N.

13. The injectable composite ink of claim 1, wherein the injectable composite ink further comprises one or more of: a plurality of cells, a plurality of genes, or a bioactive agent.

14. The injectable composite ink of claim 13, wherein the plurality of cells comprise fibroblasts.

* * * * *